US006808939B2

(12) United States Patent
Sigal et al.

(10) Patent No.: US 6,808,939 B2
(45) Date of Patent: Oct. 26, 2004

(54) ECL LABELS HAVING IMPROVED NON-SPECIFIC BINDING PROPERTIES, METHODS OF USING AND KITS CONTAINING THE SAME

(75) Inventors: George B. Sigal, Rockville, MD (US); Howie Tjiong, Holland, MI (US); Liwen Dong, Rockville, MD (US); Md. Athar Masood, Gaithersburg, MD (US); Richard C. Titmas, Boxford, MA (US)

(73) Assignees: IGEN International, Inc., Gaithersburg, MD (US); BioVeris Corporation, Gaithersburg, MD (US)

( * ) Notice: Subject to any disclaimer, the term of this patent is extended or adjusted under 35 U.S.C. 154(b) by 0 days.

(21) Appl. No.: 09/896,974

(22) Filed: Jun. 29, 2001

(65) Prior Publication Data

US 2003/0027357 A1 Feb. 6, 2003

(51) Int. Cl.[7] ..................... G01N 33/532; G01N 33/533; C07D 471/104; C07D 213/22; C12Q 1/68; C07K 1/13
(52) U.S. Cl. ..................... 436/546; 435/7.72; 435/188; 436/544; 530/391.3; 530/391.5; 530/409; 546/88; 546/257
(58) Field of Search ................... 546/88, 257; 530/409, 530/391.3, 391.5; 435/188, 7.72; 436/544, 546

(56) References Cited

U.S. PATENT DOCUMENTS

| | | | |
|---|---|---|---|
| 4,745,076 A | | 5/1988 | Müller et al. |
| 5,075,447 A | | 12/1991 | Müller et al. |
| 5,310,687 A | * | 5/1994 | Bard et al. |
| 5,324,457 A | | 6/1994 | Zhang et al. |
| 5,453,356 A | | 9/1995 | Bard et al. |
| 5,591,581 A | | 1/1997 | Massey et al. |
| 5,597,910 A | * | 1/1997 | Gudibande et al. |
| 5,695,890 A | * | 12/1997 | Thompson et al. |
| 5,958,783 A | | 9/1999 | Josel et al. |
| 5,981,286 A | | 11/1999 | Herrmann et al. |
| 6,207,369 B1 | | 3/2001 | Wohlstadter et al. |
| 6,316,607 B1 | | 11/2001 | Massey et al. |

FOREIGN PATENT DOCUMENTS

WO  WO97/32886  3/1997

OTHER PUBLICATIONS

I. Willner et al, J. Amer. Chem. Soc., 109(20), 6080–6086 (1987).*
I. Okura et al, Inorg. Chim. Acta, 101(3), L25–L26 (1985).*
N Takeyama et al, Chem. Lett., (11), 1735–1738 (1985).*
V. Penicaud et al, European J. of Organic Chemistry, (7), 1745–1748 (1999).*
A. Zaban et al, J. of Physical Chemistry B, 102(2), 452–460 (1998).*
S. Yan et al, Proceedings–Electrochemical Society, 96–9 (New Directions in Electroanalytical Chemistry, 53–64 (1996).*
S. Yan et al, J. of Physical Chemistry, 100(17), 6867–6870 (1996).*
S. Yan et al, J. of Physical Chemistry B, 101(9), 1493–1495 (1997).*
G. Will et al, J. of Physical Chemistry B, 103(38), 8067–8079 (1999).*
Fraser, C. L., et al., "Synthesis of Halomethyl and Other Bipyridine Derivatives by Reaction of 4,4'–Bis[(trimethylsilyl)methyl]–2,2'–bipyridine with Electrophiles in the Presence of Fluoride Ion", J. Org. Chem. 62: 9314–17 (1997).
Montalti, M., et al., "Luminescent Ruthenium(II) Bipyridyl–Phosphonic Acid Complexes: pH Dependent Photophysical Behavior and Quenching with Divalent Metal Ions", Inorg. Chem. 39: 76–84 (2000).
Anderson, S., et al., "Upon the Synthesis of Tris(2,2'–bipyridine)ruthenium(II) Salts and Related Complexes", J. Chem. Res. (S) 74–5 (1979).

* cited by examiner

Primary Examiner—Mary E. Ceperley
(74) Attorney, Agent, or Firm—Finnegan, Henderson, Farabow, Garrett & Dunner, L.L.P.

(57) ABSTRACT

Bipyridine or phenanthroline ligands presenting functional groups that prevent non-specific binding (in particular, negatively charged functional groups that are unaffected by standard conditions for conjugating biological reagents through amide bonds) are described as are luminescent metal complexes comprising these ligands. The use of luminescent ruthenium and osmium complexes comprising these ligands in electrochemiluminescence assays shows that the use of these labels can significantly reduce the amount of non-specific binding observed relative to assays carried out using reagents labeled with analogous labels that don't present functional groups that decrease non-specific binding.

94 Claims, 3 Drawing Sheets

ECL LABELS HAVING IMPROVED NON-SPECIFIC BINDING PROPERTIES, METHODS OF USING AND KITS CONTAINING THE SAME

CROSS-REFERENCE TO RELATED APPLICATIONS

Reference is made to the following issued patents: U.S. Pat. Nos. 5,310,687; 5,591,581; 5,597,910; 5,705,402; 5,846,485; 6,066,448; 6,214,552; and 6,207,369. The disclosure of each of these references is hereby incorporated by reference.

FIELD OF INVENTION

The present invention relates to labels, preferably metal-containing labels for use in assays. In particular, the invention relates to metal labels having ligands substituted with hydrophilic and/or charged groups that prevent the non-specific binding ("NSB") of labeled substances to other materials. The invention also relates to methods for conducting assays, preferably luminescence assays, that use these labels and to kits and compositions containing these labels.

BACKGROUND OF THE INVENTION

Documents cited in this application relate to the state-of-the-art to which this invention pertains. The disclosures of each of these references are incorporated herein by reference.

Electrochemiluminescence (ECL) detection has become an important analytical technique and has been applied in general analysis and diagnostic procedures. Electrochemiluminescence involves electrogenerated species and the emission of light. For example, electrochemiluminescence may involve luminescence generated by a process in which one or more reactants are generated electrochemically and undergo one or more chemical reactions to produce species that emits light, preferably repeatedly.

In practice, most ECL-based assays involve the use of electrochemiluminescent compounds as labels. The presence of a labeled substance or the participation of a labeled substance in a binding reaction is determined via detection of electrochemiluminescence from the ECL label. Assays for analytes based on the use of labeled binding reagents specific for an analyte of interest may be homogenous in nature (see U.S. Pat. No. 5,591,581 and Published PCT Application WO87/06706) or may involve binding reactions occurring on a solid phase such as a magnetic particle (see U.S. Pat. No. 5,705,402) or an electrode surface (see U.S. Pat. Nos. 6,066,448 and 6,207,369 and Published PCT Application WO98/12539).

An important class of ECL labels is organometallic complexes of ruthenium, osmium or rhenium having one or more polydentate heterocyclic nitrogen containing ligands (e.g., bipyridine, phenanthroline, bipyrazine, bipyrimidine, etc., or substituted derivatives thereof) such as those described in U.S. Pat. Nos. 5,310,687; 5,597,910; and 5,591,581 and Published PCT Application WO87/06706. These types of labels (in particular, labels based on tris-bipyridyl ruthenium complexes) have found considerable use because of their stability and the efficiency at which they produce ECL.

In commercial ECL instrumentation, ECL from these labels is typically produced by oxidizing the labels in the presence of an ECL coreactant, such as tripropylamine. The ECL coreactant is also oxidized at the electrode to produce a strong reductant (see, e.g., U.S. Pat. No. 5,846,485). The highly energetic reaction of the reductant and the oxidized label leads to reduction and excitation of the label to a luminescent excited state. Emission of a photon regenerates the label in its original state and allows for detection of the label.

Electrochemiluminescence is an extremely sensitive detection technique. The sensitivity of the detection technique is often, however, not the determining factor for the sensitivity of a particular assay. In assays that involve the specific binding interaction between a labeled binding reagent and a binding partner (e.g., an analyte), the sensitivity is often limited by the background signal resulting from the non-specific binding (NSB) of the labeled binding reagent with substances other than the binding partner, e.g., other components of crude samples, other assay reagents, or in the case of solid phase binding assays, the solid phase itself. In some cases, NSB may also lead to a lowering of signals through loss of reagent on the surfaces of containers, pipettes, etc. While ECL labels generally have better NSB properties than other classes of labels, under certain conditions NSB may be a limiting factor in assay sensitivity. This occurs, for example, in i) ECL assays using labeled binding reagents, where the binding reagent itself exhibits high levels of NSB; ii) ECL assays using binding reagents labeled with large numbers of labels and iii) ECL assays carried out using low concentrations of blockers of NSB (such as blocking proteins or detergents) or carried out in the absence of such blockers.

SUMMARY OF THE INVENTION

The present invention relates to substituted bipyridines and phenanthrolines having at least one and preferably two substituents, the substituents comprising negatively charged groups, preferably sulfate or sulfonate groups. These substituted bipyridines and phenanthrolines, when present as a ligand in a metal complex, reduce the NSB of the complex relative to analogous unsubstituted bipyridines or phenanthrolines. In addition, the present invention relates to organometallic complexes comprising such ligands and labeled assay reagents comprising such organometallic complexes.

The present invention also relates to luminescent metal complexes having the structure

wherein
M is Os or Ru;
$L^1$ is $L^2$ as described below or a substituted bipyridine or phenanthroline ligand having at least one substituent that is covalently linked to i) a biological material and/or an assay reagent useful in an assay or ii) a moiety that can participate in a reaction with a biological material and/or an assay reagent useful in an assay so as to form such a covalent linkage; and
$L^2$ is a substituted bipyridine or phenanthroline ligand that comprises a negatively charged group, preferably a sulfate or sulfonate group, said group acting to reduce the NSB of the complex relative the analogous complex in which $L^2$ is unsubstituted bipyridine or phenanthroline. Alternatively, $L^2$ is a substituted bipyridine or phenanthroline ligand that comprises a neutral hydrophilic group, preferably a hydroxyl group or a carboxamide, or a positively charged group, preferably, a guanidinium group.

The present invention also relates to luminescent metal complexes having the structure $ML^1L^2_2$ wherein M is Os or Ru;

$L^2$ is a metal ligand selected from the group consisting of:

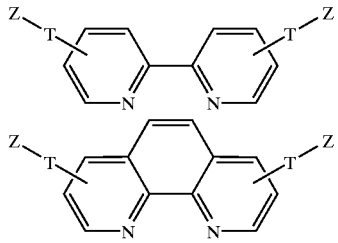

and wherein,

T is a linker group comprising an alkyl, alkenyl, alkynyl or phenyl linker, or a combination thereof, having, optionally, one or more chain carbons substituted by a heteroatom;

Z is $-SO_3^-$, $-SO_3H$, $-OSO_3^-$, $-OSO_3H$, $-PO_3^{2-}$, $-PO_3H^-$, $-PO_3H_2$, $-OPO_3^{2-}$, $-OPO_3H^-$, $-OPO_3H_2$, $-OP(R)O_2^-$, $-OP(R)O_2H$, $-[NHC(NH_2)_2]^+$, or $-NHC(NH)NH_2$; and R is alkyl; and $L^1$ is a substituted bipyridine or phenanthroline ligand having at least one substituent that is covalently linked to i) a biological material and/or a binding reagent useful in an assay or ii) a moiety that can participate in a reaction with a biological material and/or a binding reagent useful in an assay so as to form such a covalent linkage; and $L^1$ is, preferably, selected from the group consisting of

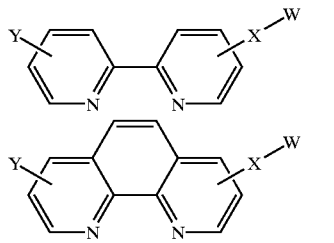

and wherein,

X is a linker group comprising an alkyl, alkenyl, alkynyl or phenyl linker, or a combination thereof, having, optionally, one or more chain carbons substituted by a heteroatom;

Y is H or alkyl and

W is a functional group that is linked to a biological molecule, binding reagent, enzyme substrate or other assay reagent or W is a functional group that when present on the ligand is suitable for conjugating the ligand to a biological material, binding reagent, enzyme substrate or other assay reagent.

The present invention also relates to labeled materials having one or more metal complexes of the invention, preferably luminescent metal complexes, linked to a material. In one embodiment, the invention relates to labeled materials having the structure $[A]_i[B]_j$, wherein A is a luminescent metal complex of the invention, B is a substance (preferably a biological material and/or an assay reagent useful in an assay) covalently linked to one or more A, i is an integer greater than zero and j is an integer greater than zero (preferably, one). Preferably, A is a metal complex with the structure $ML^1L^2_2$ as described above and A and B are covalently linked via a functional group on $L^1$.

The present invention also relates to the use of the luminescent metal complexes of the invention for the generation of luminescence. The complexes may be used in luminescence-based assays such as assays based on the measurement of photoluminescence intensity, time resolved photoluminescence, luminescence energy transfer, luminescence quenching, luminescence lifetime, luminescence polarization, chemiluminescence or, preferably, electrochemiluminescence. The invention also includes the use of complexes of the invention in non-luminescent assays such as electrochemical assays (i.e., assays involving the measurement of current or voltage associated with the oxidation or reduction of the complexes) including electrochemical assays that use the metal complex as a redox label and electrochemical assays that use the metal complex as a redox mediator for measuring the reduction or oxidation of an analyte (e.g., DNA). Preferably, the use of the metal complexes of the invention leads to improved assay performance through low non-specific binding of the complex relative to analogous complexes not presenting low NSB functional groups.

The present invention also relates to methods of measuring the labeled materials of the invention comprising the steps of i) contacting the labeled materials with a binding reagent and, optionally, a solid phase support; ii) forming a binding complex comprising the binding reagent, the labeled materials, and, optionally, the solid phase support; iii) inducing the labeled materials to produce a signal, preferably, luminescence, more preferably ECL and iv) measuring the signal so as to measure the luminescent metal complex. Preferably, the use of the metal complexes of the invention leads to improved assay performance through low non-specific binding of the metal complex relative to analogous metal complexes not presenting low NSB functional groups.

The present invention also relates to methods of measuring an analyte in a sample comprising the steps of i) contacting the sample with a labeled binding reagent and optionally a solid phase support; ii) forming a binding complex comprising the binding reagent, the analyte and, optionally, the solid phase support; iii) inducing labels in the labeled binding reagent to produce a signal, preferably, luminescence, more preferably ECL and iv) measuring the signal so as to measure the analyte in the sample; wherein the labeled binding reagent comprises one or more of the low NSB labels described above covalently linked to a binding reagent specific for the analyte. Preferably, the use of the labels of the invention leads to improved assay performance through low non-specific binding of the labels relative to analogous labels not presenting low NSB functional groups.

The present invention also relates to methods of measuring an analyte in a sample comprising the steps of i) contacting the sample with a labeled analog of the analyte, a binding reagent and, optionally, a solid phase support; ii) forming a binding complex comprising the labeled analog of the analyte, the binding reagent and, optionally, the solid phase support; iii) inducing labels in the labeled analog of the analyte to produce a signal, preferably, luminescence, more preferably ECL and iv) measuring the signal so as to measure the analyte in the sample; wherein the labeled analog of the analyte comprises one or more of the low NSB labels described above covalently linked to an analog of the analyte, and wherein said analog of the analyte competes with the analyte for binding to the binding reagent. Preferably, the use of the labels of the invention leads to improved assay performance through low non-specific binding of the complex relative to analogous labels not presenting low NSB functional groups.

The present invention also relates to methods of measuring an analyte or a chemical or biological activity in a sample comprising the steps of i) contacting a sample containing the analyte or the chemical or biological activity (or a sample containing substrates or products of the activity) with a low NSB metal complex of the invention; ii) inducing the metal complex to produce a signal, preferably luminescence, more preferably electrochemiluminescence and iii) measuring the signal so as to detect or measure the chemical or biological activity.

The present invention also relates to methods of improving existing assays employing metal complexes by replacing the metal complexes or ligands on the metal complexes with the low NSB labels or ligands of the invention.

The invention further relates to kits and compositions containing the low NSB ligands and metal complexes of the invention.

DETAILED DESCRIPTION OF THE INVENTION

Figure 1:
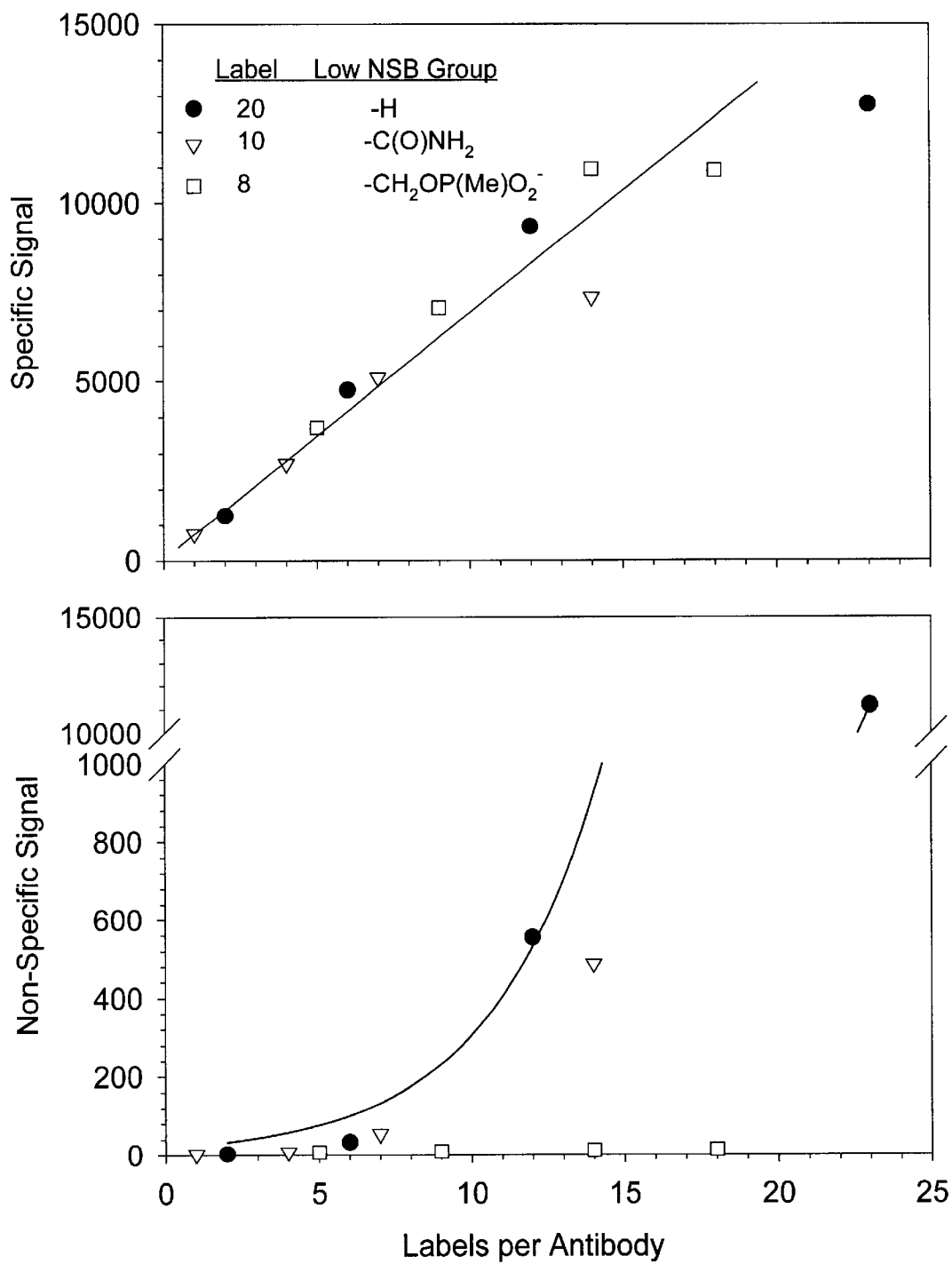
FIG. 1 shows the results of a comparison of ECL-based sandwich immunoassays on carbon composite electrodes using antibodies labeled with complexes 20, 8, and 10. The figure shows the non-specific and specific signals as a function of the number of labels per antibody.

The present invention relates to improved labels for use in assays for measuring an analyte of interest. The word "measurement" and verb forms of "to measure" as used herein refer to both quantitative and qualitative determinations. "Measurement" is understood to include the comparison of a quantity relative to one or more threshhold values or standards, as well as determinations carried out to detect the presence of something and/or the occurrence of an event (e.g., the presence of an analyte or label in a solution or the emission of luminescence). One preferred embodiment of the invention relates to luminescent organometallic complexes useful as labels in ECL assays. The complexes comprise one or more substituted phenanthroline or bipyridine metal ligands, at least one of the metal ligands having substituents that prevent non-specific binding of the ligand (such ligands are referred to hereafter as low NSB ligands). Preferred low NSB substituents comprise negatively charged groups. Negatively charged groups are understood to include neutral or positively charged groups that may be deprotonated in water to a negatively charged state (i.e., having $pK_a$s between 0 and 14). Suitable negatively charged groups include carboxylates, phosphates, phosphonates, sulfates and sulfonates (as well as their protonated forms). Preferably, the negatively charged group will not react under the conditions used to couple amines and carboxylic acids through amide bonds. Preferred negatively charged groups include sulfates and, most preferably, sulfonate groups due to their high stability, low $pK_a$, and relative insensitivity to the conditions and reagents used to couple amines and carboxylic acids to form amide bonds (e.g., a sulfonate on one ligand of a metal complex will not interfere with the use of a carbodiimide to couple a carboxylic acid on another ligand with an amine-containing reagent. Phosphates and phosphonates are also useful, although they will react with some carboxylic acid activating reagents such as carbodiimides; when these reactions occur under aqueous conditions the products of these reactions are often unstable and do not affect the final result of a conjugation reaction. In an alternate embodiment of the invention, the bipyridine or phenanthroline ligands are substituted with substituents that comprise neutral hydrophilic groups, preferably hydroxyl groups or carboxamides, or positively charged groups, preferably, guanidinium groups (such ligands are also most preferably chosen so as to be insensitive to standard conditions used to make amide bonds).

The ligands are designed so that organometallic complexes comprising the ligands will give, relative to analogous organometallic complexes comprising unsubstituted bipyridines or phenanthrolines, lower non-specific binding while, preferably, also giving comparable (within a factor of 2) or better ECL signals on a per label basis. The negatively charged groups are, preferably, not directly linked to the phenanthroline or bipyridine rings but are attached through linkers such as alkyl, alkenyl, alkynyl and/or phenyl linkers so as to not have detrimental effect on the ECL properties of organometallic complexes comprising the ligand (e.g., by affecting the redox properties, quantum yields of luminescence, energy of the excited states, or label stability). Such linkers may include heteroatoms in the linking chain or as substituents, although these heteroatoms are, preferably, not directly bonded to the bipyridine or phenanthroline rings (e.g., carbons in an alkyl linking chain may be replaced with oxygens to form one or more alkyl ether linkages or oligo-ethylene glycol linkers). Preferred linkers are phenyl and alkyl groups. Short (one to five carbon) alkyl groups are especially preferred due their relatively minor influence on ECL and their relative inability to unfold or denature proteins when incorporated in organometallic labels attached to the protein. Single carbon linkers are most preferred since they screen the bipyridine or phenanthroline moieties from the low NSB functional group while not providing additional hydrophobic surface area or substantially increasing the effective volume of the label.

The ligands are preferably disubstituted at the 5 and 5' positions or, most preferably, the 4 and 4' positions for bipyridyl ligands or the 3 and 8 or, most preferably, the 4 and 7 positions for phenanthrolyl ligands; in metal complexes, these positions have high solvent accessibility and exhibit limited steric crowding. Exemplary low NSB ligands are shown below for bipyridines substituted at the 4 and 4' positions and phenanthrolines substituted at the 4 and 7 positions. Other substitution patterns are not shown but can be defined by analogy.

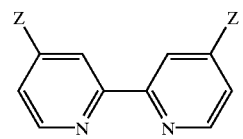 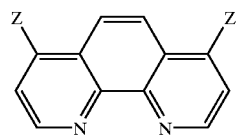

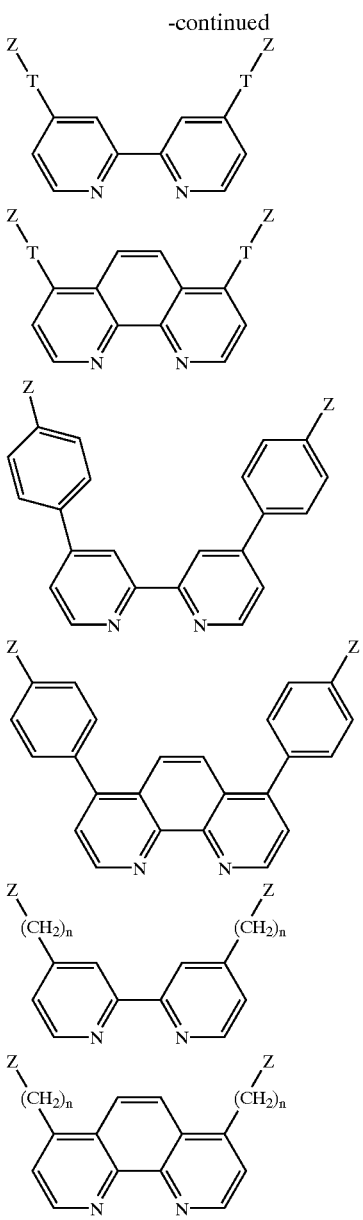

Where
- T=a linker group, preferably, an alkyl, alkenyl, alkynyl or phenyl linker or a combination thereof, optionally having one or more chain carbons replaced by a heteroatom
- Z=—$SO_3^-$, —$SO_3H$, —$OSO_3^-$, —$OSO_3H$, —$PO_3^{2-}$, —$PO_3H^-$, —$PO_3H_2$, —$OPO_3^{2-}$, —$OPO_3H^-$, —$OPO_3H_2$, —$OP(R)O_2^-$, —$OP(R)O_2H$, —[$NHC(NH_2)_2$]$^+$, or —$NHC(NH)NH_2$
- n=an integer, preferably, between 1–5, most preferably 1
- R=alkyl, preferably methyl.

The present invention relates to organometallic complexes comprising one of the aforementioned low NSB ligands chelated to a metal atom, e.g., Co, Ni, Cu, Ru, Rh, Pd, Ag, Re, Os, Ir, Pt, Fe, Tc, Cr, Mo and W. An important class of such complexes is luminescent ECL-active complexes of Ru and Os, preferably in the Ru(II) or Os(II) oxidation states. The invention includes complexes with the formula $ML^2_3$, where $L^2$ is a low NSB ligand of the invention and M is Ru or Os, preferably in the Ru(II) or Os(II) oxidation states. It is understood that notations like $ML^2_3$ or $ML^1L^2_2$, as used herein, do not exclude the complexes from having an overall net charge (as determined by the charge state of the ligands and the oxidation state of the metal) and that the complexes may be associated with counterions so as to form a composition with an overall neutral charge. The $ML^2_3$ class of complexes is especially useful in applications that use free unconjugated ECL-active compounds (see, e.g., U.S. Pat. No. 5,641,623) and should reduce adsorption of complex to most electrode surfaces.

In applications that use ECL-active complexes as labels, a particularly useful class of complexes have the formula $ML^1L^2_2$, where M is Ru or Os (preferably in the Ru(II) or Os(II) oxidation states), $L^2$ is a low NSB ligand as described above, and $L^1$ is a substituted bipyridine or phenanthroline that is covalently linked to a biological molecule, binding reagent, enzyme substrate or other assay reagent (i.e., to form a labeled reagent, where "label" refers to the metal complex component of the labeled reagent) or, alternatively, has a substituent that is capable of being covalently conjugated to a biological molecule, binding reagent, enzyme substrate or other assay reagent so as to form a labeled reagent. Such ligands may be referred to herein as linking ligands. Biological materials refers herein to materials of biological origin or synthetic analogs thereof, e.g., amino acids, nucleosides, nucleotides, proteins, peptides (and peptidomimetics), nucleic acids (as well as analogs having modified bases or unnatural linkages, e.g., PNAs), hormones, vitamins, sugars, second messengers, polysaccharides, steroids, lipids, phospholipids, cells, organelles, subcellular fragments, viruses, prions, etc. Binding reagents are reagents capable of participating in a specific binding interaction with another material. Examples of binding reagents include: enzymes, antibodies (and fragments thereof), receptors, ligands of biological receptors, metal ligands, nucleic acids, nucleic acid intercalators, nucleic acid major and minor groove binders, haptens, avidin, streptavidin, biotin, purification tags (such as FLAG, myc, glutathione S-transferase, His-tag, etc.), binding partners of purification tags (such as specific antibodies, glutathione, nitrilotriacetic acid, iminodiacetic acid, etc.), etc. Enzyme substrates include molecules that are transformed in enzyme-catalyzed reactions and include cofactors, nucleic acids that are joined or cleaved by enzymes, and peptides that are joined or cleaved by enzymes.

Examples of functional groups that when present on the ligand are suitable for conjugating the ligand to a biological material, binding reagent, enzyme substrate or other assay reagent include functional groups known in the art of conjugation chemistry such as: amines, thiols, hydrazides, carboxylic acids, activated carboxylic acids (e.g., acyl chlorides and active esters such as N-hydroxysuccinimide esters), hydroxyls, alkyl halides, isocyanates, isothiocyanates, sulfonyl chlorides, activated phosphates, phosphonates or phosphoramidites, alkenes, alkynes, active carbamates and carbonates, aldehydes, ketones, maleimides, disulfides, α,β unsaturated carbonyls, carbon linked to leaving groups such as halides, mesyl, tosyl, tresyl, etc. For further information on useful functional groups for conjugating labels to reagents and useful conjugation techniques, the reader is directed to G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996), these references hereby incorporated by reference. Preferred functional groups include amines, carboxylic acids, active esters and, most preferably, N-hydroxy succinimide esters.

Preferably, such functional groups are linked to a bipyridine or phenanthroline ring via a linker chain comprising alkyl, alkenyl, alkynyl and/or phenyl groups so as to limit the effect of the functional group on ECL. Such linkers may include heteroatoms in the linking chain or as substituents, although these heteroatoms are, preferably, not directly bonded to the bipyridine or phenanthroline rings (e.g., carbons in an alkyl linking chain may be replaced with oxygens to form alkyl ethers or oligo(ethylene glycol linkers). The ligands are preferably substituted at the 5 and/or 5' positions or most preferably at the 4 and/or 4' positions for bipyridyl ligands or preferably substituted at the 3 and/or 8 or most preferably at the 4 and/or 7 positions for phenanthrolyl ligands; in metal complexes, these positions exhibit limited steric crowding. Examples of suitable linking ligands are shown below. The ligands are shown as being substituted at the 4 and 4' positions for bipyridine or the 4 and 7 positions for phenanthroline, however, the structures of ligands with other substitution patterns are clear by analogy.

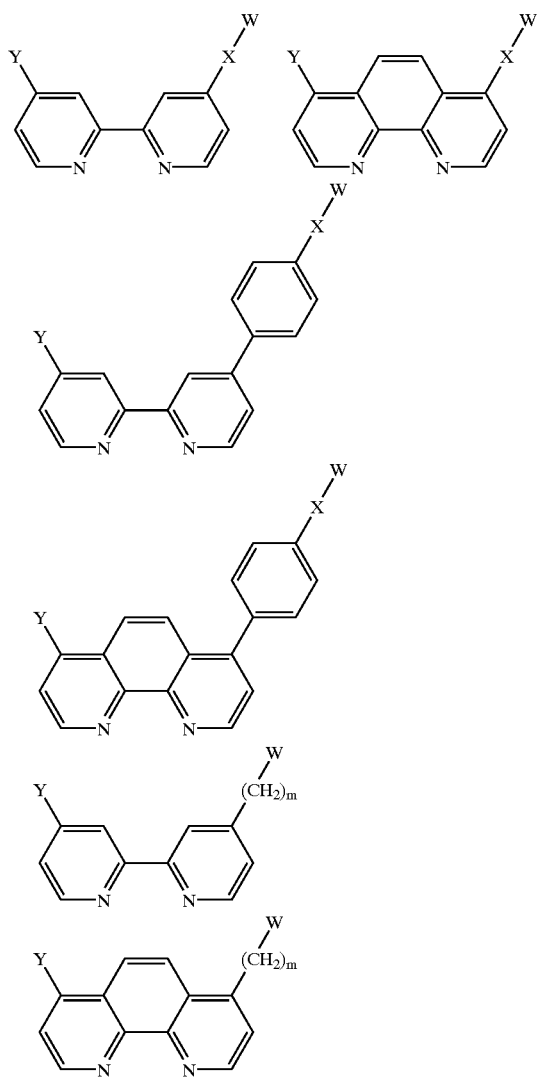

Where
X = a linker group, preferably, an alkyl, alkenyl, alkynyl or phenyl linker or a combination thereof, optionally having a chain carbon replaced by a heteroatom Y = H, or alkyl, preferably, $-CH_3$ W = a functional group that is linked to a biological molecule, binding reagent, enzyme substrate or other assay reagent or a functional group that when present on the ligand is suitable for conjugating the ligand to a biological material, binding reagent, enzyme substrate or other assay reagent m = an integer, preferably, between 1–5

In some embodiments of the invention, the labels of the invention are covalently linked to another substance (e.g., a biological material, binding reagent, enzyme substrate or other assay reagent) and are used as labels to allow the measurement of the substance. A preferred embodiment relates to labeled materials having the structure $[A]_i[B]_j$, wherein A is a luminescent metal complex of the invention, B is a substance (preferably, a biological material, binding reagent, enzyme substrate or other assay reagent) covalently linked to one or more A, i is an integer greater than zero and j is an integer greater than zero (preferably, one). The covalent linkage may be provided by a variety of covalent linkages known in the art of conjugation chemistry, e.g., amide bonds, amine linkages, ethers, thioethers, carbamates, ureas, thioureas, Schiff's Bases, carbon-carbon bonds, esters, phosphate esters, sulfonamides, etc. Most preferably, A is a metal complex with the structure $ML^1L^2_2$, wherein M is Ru or Os (preferably in the Ru(II) or Os(II) oxidation states), $L^2$ is a low NSB ligand of the invention as described above and A and B are covalently linked via a functional group on a linking ligand $L^1$ as described above. Another embodiment of the invention relates to a labeled substance with the structure $ML^1L^2_2$, wherein M is Ru or Os (preferably in the Ru(II) or Os(II) oxidation states), $L^2$ is a low NSB ligand of the invention and $L^1$ is a linking ligand that is linked to another substance (preferably, a biological material, binding reagent, enzyme substrate or other assay reagent). Examples of suitable $L^1$ according to this aspect of the invention are shown below. The ligands are shown as being substituted at the 4 and 4' positions for bipyridine or the 4 and 7 positions for phenanthroline, however, the structures of ligands with other substitution patterns are clear by analogy.

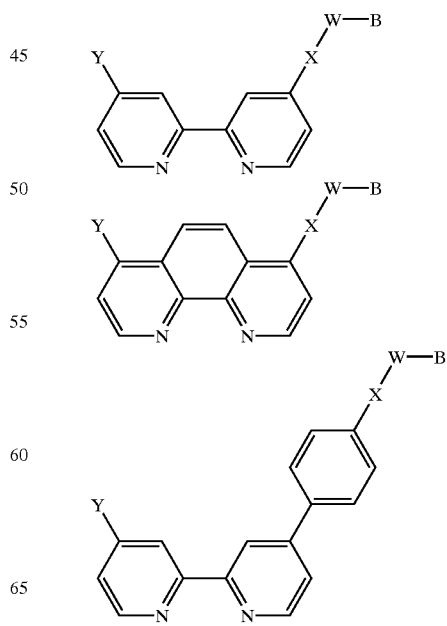

-continued

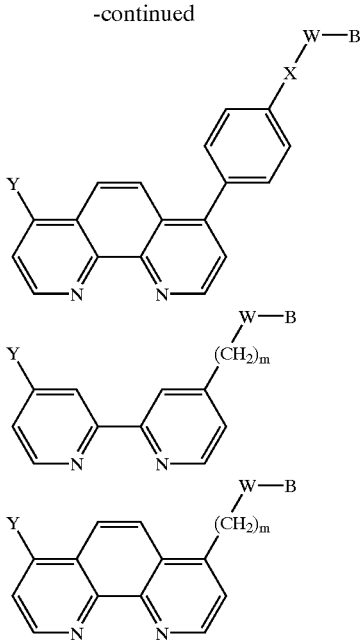

Where
X=a linker group, preferably, an alkyl, alkenyl, alkynyl or phenyl linker or a combination thereof, optionally having a chain carbon replaced by a heteroatom
Y=H, or alkyl, preferably, —$CH_3$
B=a substance, preferably, a biological molecule, binding reagent, enzyme substrate or other assay reagent
W=a functional group that is linked to B
m=an integer, preferably, between 1–5

Additional embodiments of the invention include luminescent Re(I) complexes comprising the low NSB ligands of the invention, e.g., Re(I)(CO)$_3$L$^3$L$^2$, where L$^2$ is a low NSB ligand of the invention as defined above, preferably presenting negative charged functional groups, more preferably presenting sulfate groups and most preferably presenting sulfonate groups and L$^3$ is a monovalent ligand of Re, such as a halide ion, CO, an organic isonitrile, an alkynyl group, a nitrogen-containing heterocycle, pyridine or a substituted pyridine. Preferably, L$^3$ is a monovalent ligand of Re that is linked to a biological molecule, binding reagent, enzyme substrate or other assay reagent or a functional group that when present on the ligand is suitable for conjugating the ligand to a biological material, binding reagent, enzyme substrate or other assay reagent (such reagents, linkages and functional groups having the properties as described for the Ru and Os complexes). L$^3$ is most preferably a substituted isonitrile or pyridine, the pyridine preferably being substituted at the 3 or 4 positions.

The labels and labeled materials of the invention are useful in a wide variety of known assay formats employing metal complexes, preferably, luminescent metal complexes, e.g., assays based on the measurement of photoluminescence intensity, time resolved photoluminescence, luminescence energy transfer, luminescence quenching, luminescence lifetime, luminescence polarization, chemiluminescence or, preferably, electrochemiluminescence. For examples of methods for conducting ECL assays, the reader is directed towards U.S. Pat. Nos. 5,591,581; 5,641,623; 5,643,713; 5,705,402; 6,066,448; 6,165,708; 6,207,369; and 6,214,552 and Published PCT Applications WO87/06706 and WO98/12539, these references hereby incorporated by reference. Preferably, the use of the luminescent metal complexes of the invention leads to improved assay performance through low non-specific binding of the complex relative to analogous complexes not presenting low NSB functional groups. The use of the luminescent metal complexes, preferably, leads to an improvement in a given assay in the ratio of specific to non-specific signal of greater than or equal to a factor of two, or more preferably, greater than or equal to a factor of 5.

In some applications, the luminescent metal complexes of the invention are used as labels to allow the monitoring of assay reagents such as enzyme substrates or binding reagents. We have found that reagents labeled with the luminescent metal complexes of the invention (especially complexes presenting negatively charged groups) show significant decreases in non-specific binding relative to reagents labeled with analogous complexes that do not present low NSB functional groups. The use of the luminescent metal complexes of the invention significantly reduces the requirement for blocking reagents to reduce non-specific binding, reduces the loss of reagents on the surfaces of containers and fluidic lines, and reduces non-specific signals due to non-specific interactions of labeled binding reagents. These effects are most pronounced when reagents, e.g., antibodies and other proteins, are linked to multiple labels. We have prepared reagents linked to 4–7, 7–10, 10–15, 15–20 and greater than 20 labels and observed only minor amounts of non-specific binding. By going to higher numbers of labels per reagent, assay signals may be increased (relative to assays using luminescent metal complexes not presenting low NSB functional groups) 2–5 fold, 5–10 fold, or greater, while maintaining equivalent or significantly improved ratios of specific to non-specific signals. Alternatively, under conditions that give equivalent specific signals, the ratio of specific to non-specific signal is greatly improved.

Many assay formats employ solid-phase supports so as to couple the measurement of an analyte or activity to the separation of labeled reagents into solution-phase and solid phase supported portions. Examples include solid-phase binding assays that measure the formation of a complex of a material and its specific binding partner (one of the pair being immobilized, or capable of being immobilized, on the solid phase support), the formation of sandwich complexes (including a capture reagent that is immobilized, or capable of being immobilized, on the solid phase support), the competition of two competitors for a binding partner (the binding partner or one of the competitors being immobilized, or capable of being immobilized, on the solid phase support), the enzymatic or chemical cleavage of a label (or labeled material) from a reagent that is immobilized, or capable of being immobilized on a solid phase support and the enzymatic or chemical attachment of a label (or labeled material) to a reagent that is immobilized or capable of being immobilized on a solid-phase support. The amount of analyte or activity is determined by measuring the amount of label on the solid phase support and/or in solution, measurements typically being conducted via a surface selective technique, a solution selective technique, or after separation of the two phases. The term "capable of being immobilized" is used herein to refer to reagents that may participate in reactions in solution and subsequently be captured on a solid phase during or prior to the detection step. For example, the reagent may be captured using a specific binding partner of the reagent that is immobilized on the solid phase. Alternatively, the reagent is linked to a capture moiety and a specific binding partner of the capture moiety is immobilized on the solid phase. Examples of useful capture moiety-binding partner pairs include biotin-streptavidin (or avidin), antibody-hapten, receptor-ligand, nucleic acid—complementary nucleic acid, etc.

It is particularly important in solid phase binding assays that labeled reagents do not bind non-specifically to the solid phase because that binding can result in non-specific signal and significantly reduce the sensitivity of assays. We have tested reagents labeled with labels of the invention in ECL assays using magnetic particles as solid phase supports and ECL assays using electrodes as solid phase supports. In both cases, comparisons to assays using labels that do not present low NSB functional groups showed that assays using the labels of the invention could be optimized to work with more heavily labeled reagents (e.g., 4–7, 7–10, 10–15, 15–20 and greater than 20 labels per reagent), to give higher signals (e.g., 2–5 fold, 5–10 fold, or greater improvements) and to produce higher ratios of specific to non-specific signals (e.g., 1–2 fold, 2–5 fold or greater than 5-fold improvements). The labels of the invention have proved to be particularly beneficial in preventing the non-specific binding of labels and labeled reagents to carbon-containing electrodes used as supports for solid phase assays and/or as electrodes for inducing ECL. Such electrodes include electrodes comprising carbon fibrils or other carbon particles such as plastic composite electrodes comprising carbon fibrils or carbon particles dispersed in a polymeric matrix. Beneficial effects have also been observed in assays carried out on electrodes comprising a thin layer of carbon ink supported on a support (as described in copending application ____ entitled "Assay Plates, Reader Systems and Methods for Luminescence Test Measurements", filed on even date, hereby incorporated by reference).

Another aspect of the invention relates to kits for use in conducting assays, preferably luminescence assays, more preferably electrochemiluminescence assays, comprising the ligands and/or metal complexes of the invention and at least one assay component selected from the group consisting of: (a) at least one electrochemiluminescence coreactant; (b) one or more binding reagents; (c) one or more pH buffers; (d) one or more blocking reagents; (e) one or more preservatives; (f) one or more stabilizing agents; (g) one or more enzymes; (h) one or more enzyme substrates; (i) one or more magnetic particles; (j) one or more electrodes suitable for inducing ECL and (k) one or more detergents. Preferably, at least one of said assay components is covalently linked to a ligand or metal complex of the invention.

Preferably, the kit comprises the ligands and/or metal complexes of the invention and at least one assay component(s) in one or more, preferably two or more, more preferably three or more containers.

According to one embodiment, the kit comprises the ligands and/or metal complexes of the invention and one or more of the assay components in one or more containers in dry form.

According to one embodiment, the ligands and/or metal complexes of the invention and assay components are in separate containers.

One preferred embodiment relates to a kit for use in conducting electrochemiluminescence assays comprising at least one label according to the invention and at least one electrochemiluminescence coreactant.

According to one preferred embodiment, the kit comprises the label of the invention and further comprises at least one bioreagent selected from: antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents or combinations thereof.

Another aspect of the invention relates to compositions comprising the metal ligand or metal complex of the invention attached to an assay-performance substance.

One embodiment of the invention relates to a composition for the detection of an analyte of interest present in a sample, which composition comprises:

(i) the metal complex of the invention containing a functional group and (ii) an assay-performance-substance linked to said functional group, said assay-performance-substance being capable of binding to the analyte-of-interest or being bound to the analyte-of-interest.

Preferably, the composition further comprises at least one substance selected from the group consisting of (i) added analyte of interest or added analogue of said analyte;

(ii) a binding partner of said analyte or a binding partner of said analogue; and (iii) a reactive component capable of binding with (i) or (ii).

Yet another embodiment of the invention relates to a composition for the detection of an analyte of interest present in a sample, which composition comprises:

(a) the metal complex of the invention and (b) an assay-performance-substance linked to said complex, wherein said assay-performance-substance contains at least one substance selected from the group consisting of:

(i) added analyte of interest or added analogue of said analyte;

(ii) a binding partner of said analyte or a binding partner of an analogue of said analyte; and (iii) a reactive component capable of binding with (i) or (ii).

A still further embodiment of the invention relates to a composition of matter for use as a reagent in an assay comprising the metal ligand or metal complex of the invention bound to an assay-performance-substance and at least one other component selected from the group consisting of:

(a) electrolyte;

(b) analyte of interest or an analog of the analyte of interest;

(c) a binding partner of the analyte of interest or of its analog;

(d) a reactive component capable of reacting with (b) or (c); and (e) an ECL coreactant and provided, however, that no two components contained within any reagent composition are reactive with one another during storage so as to impair their function in the intended assay.

EXAMPLES

ECL Instrumentation

ECL examples presented here were conducted on a variety of ECL instrumentation. Some methods used magnetic particles as solid phase supports for binding assays as described in U.S. Pat. Nos. 5,935,779; 6,133,043; and 6,200,531. Such ECL measurements involve the collection of the magnetic particles on a platinum electrode, applying electrical energy to the electrode and measuring the emitted luminescence. Other examples employed composite electrodes comprising carbon fibrils dispersed in a polymeric matrix as both the solid phase support for binding assays and the electrode for the induction of ECL (as described in U.S. Pat. No. 6,207,369 and Published PCT Application WO98/

12539). The descriptions of ECL methods and instrumentation in the references listed above are hereby incorporated by reference. Because of differences in electrodes, instrumentation, light detectors, detector gains, etc., the ECL signals reported in the different examples should not be directly compared.

Example 1

Synthesis of Ligand 1

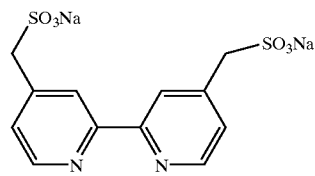

Sodium sulfite (1.3 g) was added to a suspension containing 1.7 g of 4,4'-bis-bromomethylbipyridine (Fraser et al., *J. Org. Chem.* 1997, 62, 9314–9317) in 250 mL of a 7:3 water/methanol mixture. The mixture was refluxed for 60 min, cooled, and then concentrated to ~50% of its original volume by rotary evaporation. The remaining aqueous solution was washed with 2×20 mL of ethyl acetate. The aqueous phase was concentrated to dryness by rotary evaporation. The remaining solid material was further dried under high vacuum. The product was extracted from the solid material into 3×100 mL portions of boiling 1% water/methanol (by stirring the solid in each portion for 5 min before collecting the supernatant by filtration). The filtrates were combined and concentrated by rotary evaporation to give a crude solid product. The product was purified by recrystallization from water/isopropanol and washed with 1:4 water/isopropanol, isopropanol and ether to give a pure white solid. Typical yields are ~50% but may be improved by recovering product from the recrystallization supernatant.

Example 2

Synthesis of Complex 2

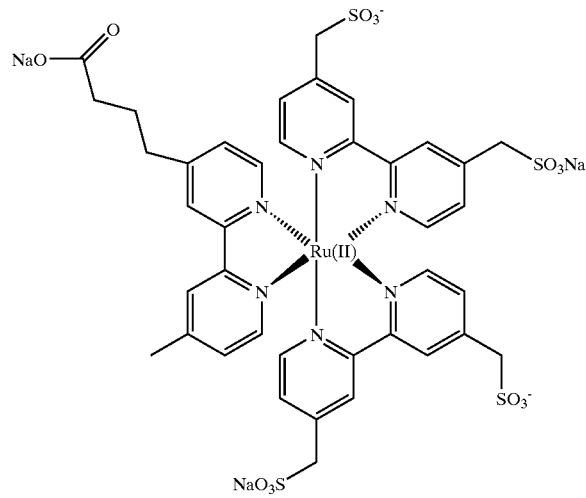

The first step of the synthesis involved preparing the complex of the ligand 4-(4-methyl-2,2-bipyridine-4'-yl)-butyric acid with $RuCl_3$ by a modification of the procedure of Anderson et al. (*J. Chem. Research* (S) 1979, 74–75). $RuCl_3$ hydrate (0.94 g) was combined with 4 mL of 1N HCl and 8 mL of water and dissolved by vigorous mixing. While mixing the resulting solution, 1.02 g of the ligand 4-(4-methyl-2,2-bipyridine-4'-yl)-butyric acid (Published PCT Application No. WO87/06706) was added. The mixture was mixed vigorously for 36 hours during which time the ligand-$RuCl_3$ complex precipitated from solution. The product suspension was cooled and the product collected by filtration, washed with 1 N HCl, water and ether, and dried under vacuum. Typical yields were about 60%.

The resulting complex (0.47 g) was combined with 0.78 g of the sulfonate-containing bipyridine ligand 1 in 75 mL of ethylene glycol. The solution was refluxed and monitored by visible adsorption at 455 nm to determine when product formation was complete (less than 2.5 hours). The solvent was removed by rotary evaporation (using a bath temperature<100 C.) and the residue was dissolved in 15 mL of 1 N NaOH and incubated in the dark for 2 hours to hydrolyze any esters that may have formed during the formation of the complex. The solution was diluted to 750 mL with 10 mM formic acid and loaded on a 100 mL column of QAE-Sephadex A-25 (previously equilibrated with 500 mM NaCl, 10 mM formic acid and then washed with copious amounts of 10 mM formic acid). The product was eluted using a gradient of 0–250 mM NaCl in 10 mM formic acid. The product fraction was concentrated by rotary evaporation. Most of the salt was removed by extracting the solid product into 5×10 mL of cold methanol (with the addition of a small amount of water if necessary), concentrating the extract and repeating the extraction procedure one more time. The product was then purified on reverse phase silica using 5:95:0.1 acetonitrile/water/trifluoroacetic acid as the eluent. The reverse phase purified product was dissolved in ~2 mL of water and the pH adjusted to 6–8 with 1 N NaOH. The resulting solution was applied to a 100 mL column of Sephadex G-15 and eluted with water. The product fraction was lyophilized to give the product as a pure orange solid. Typical yields were ~50%. The three chromatography steps could be replaced with a single purification on QAE-Sephadex A-25 by using a gradient of a volatile salt such as ammonium acetate.

Example 3

Synthesis of Complex 3

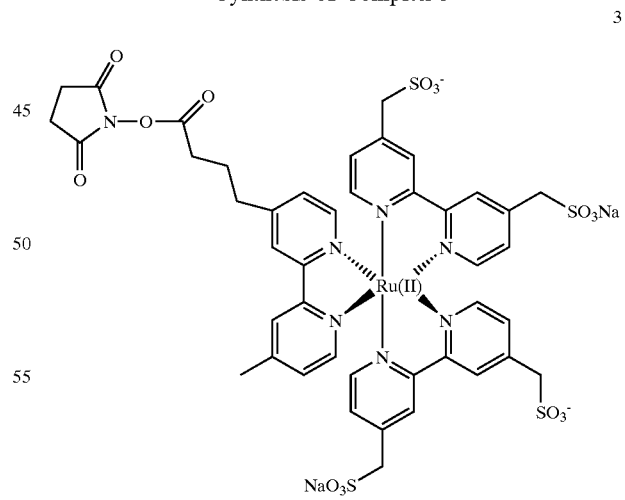

Complex 2 was activated as the NHS ester by the following procedure. Complex 2 (22 mg) was dissolved in 1 mL of 40 mM HCl. While mixing, 5.8 mg of N-hydroxy succinimide (NHS) was added followed by 39 mg of N-ethyl-N'-(3-dimethylaminopropyl)-carbodiimide (EDC). The reaction was allowed to incubate for 30 min at room temperature after which it was immediately passed through a 30 mL column of Sephadex G-15 (preequilibrated at 4 C.

Example 4

Synthesis of Ligand 7

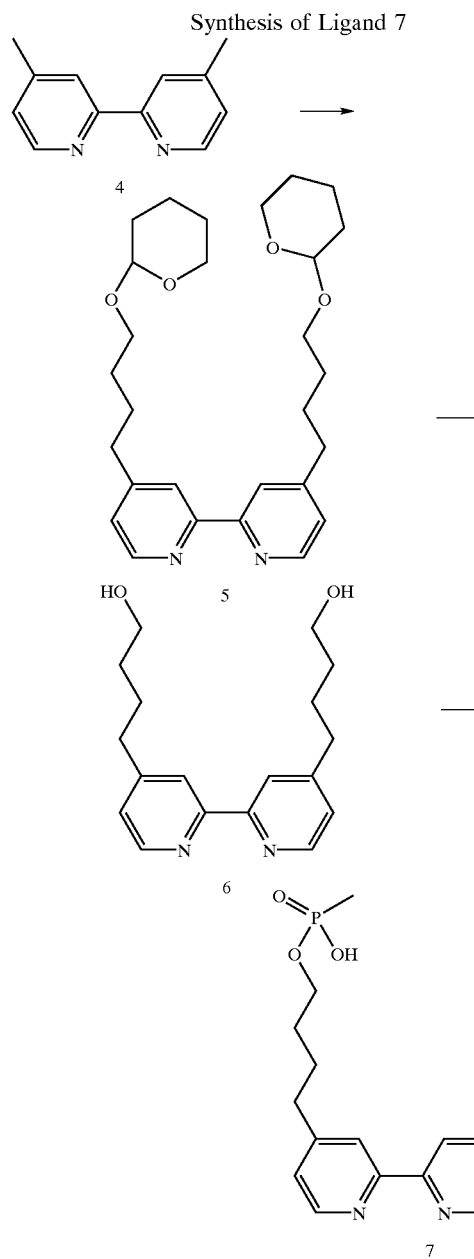

Intermediate 5 was prepared from compound 4 in two separate alkylation steps. A solution was prepared containing 1.38 g of 4,4-dimethyl-2,2-bipyridine in 60 mL of dry THF under inert atmosphere and cooled to 0 C. Added 5.25 mL of lithium diisopropylamine (LDA, 1.5 M solution in cyclohexane) dropwise with stirring and incubated for 30 min at 0 C. Added 1.4 mL of 2-(3-bromopropyloxy) tetrahydro-2H-pyran and incubated 3 hrs more at 0 C. The reaction was quenched with sat'd $NH_4Cl$ and concentrated under reduced pressure to remove THF. The remaining aqueous solution was extracted with methylene chloride. The organic fractions were dried over $MgSO_4$, concentrated, and purified by silica chromatography using 4% methanol/ methylene chloride as the eluent to the mono-alkylated product in 95% yield. The mono-alkylated product (1.925 g) was dissolved in dry THF and reacted with 4 mL of LDA and 1.05 mL of 2-(3-bromopropyloxy)tetrahydro-2H-pyran under the conditions used for the first alkylation. The reaction was worked up by quenching with sat'd $NH_4Cl$, adjusting the pH to ~8 with potassium carbonate, extracting the product into methylene chloride, drying over $MgSO_4$ and purifying by chromatography on basic alumina (activity I) using 10% ethyl acetate/hexane as eluent. The overall yield of the dialylated intermediate 5 from starting material 4 was 73%.

The intermediate 5 was deprotected to give diol 6 under acidic conditions. Intermediate 5 (1.277 g) was dissolved in 17 mL of 1:1 1 N HCl/methanol. The solution was incubated overnight at room temperature. The pH of the solution was adjusted to ~9 with concentrated ammonium hydroxide and the product was extracted into methylene chloride, dried over $MgSO_4$, and purified by chromatography over basic alumina using 3% methanol/methylene chloride as the eluent. The diol 6 was collected in 84% yield.

Preparation of the diphosphonate ester 7 was achieved by reacting the diol 6 with methyldichlorophospite. Diol 6 (60 mg) was dissolved in ~8 mL of pyridine. Most of the pyridine was distilled off leaving ~1 mL of solution. The remaining solution was added dropwise with stirring to a chilled (0 C.) solution containing 106 mg of methydichlo-rophosphite in 0.5 mL of methylene chloride. The reaction was allowed to proceed for 45 min at 0 C. The reaction was quenched by the addition of 2 mL of 2 M potassium carbonate. The solution was concentrated to dryness by rotary evaporation. Water was added and evaporated off several times to remove all the pyridine. The product was purified by HPLC chromatography on a C18 reverse phase column using a gradient of acetonitrile in water containing 0.1% trifluoracetic acid (TFA).

Example 5

Synthesis of Complex 8

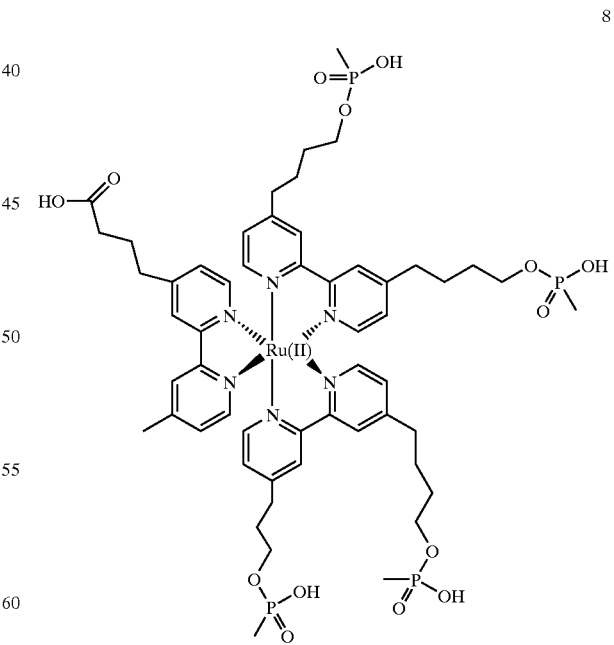

Complex 8 was prepared from ligand 7, the ligand 4-(4-methyl-2,2-bipyridine-4'-yl)-butyric acid and $RuCl_3$ by a procedure analogous to that used to prepare complex 2 from ligand 1. Purification was achieved by chromatography on

Example 6

Synthesis of Ligand 9

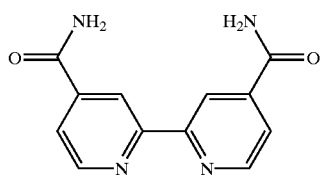

A suspension containing 1.02 g of 4,4'-dicarboxy-2,2'-bipyridine dimethyl ester in 200 mL of methanol was heated to boiling to dissolve as much of the dimethyl ester as possible. After allowing the solution to cool to room temperature, ammonia gas was bubbled into the solution. The reaction was allowed to proceed until TLC showed the disappearance of the starting material. The insoluble product 9 was collected by filtration.

Example 7

Synthesis of Complex 10

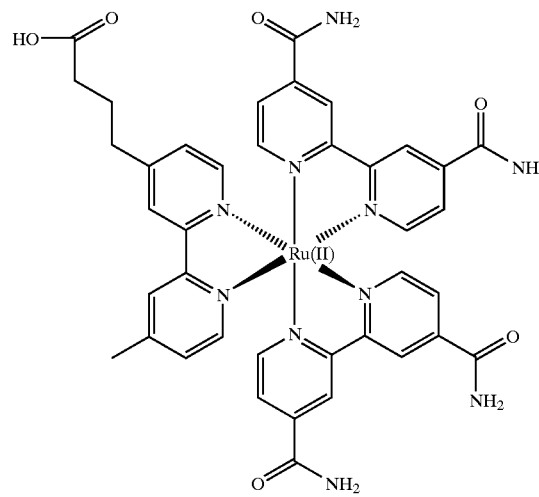

Ligand 9 (300 mg) was combined with 162 mg of $RuCl_3$ hydrate in DMF and refluxed overnight. The insoluble $RuL_2Cl_2$ intermediate was collected by filtration and washed with acetone and water. A portion of the intermediate (49.8 mg) was combined with 21.8 mg of the ligand 4-(4-methyl-2,2-bipyridine-4'-yl)-butyric acid in ~100–150 mL of 1:1 methanol/water and the mixture was refluxed overnight. The resulting solution was decanted to remove insoluble impurities and concentrated by rotary evaporation. Purification was achieved by silica chromatography using methanol saturated with NaCl as the eluent. After removal of the solvent by rotary evaporation, the product was dissolved in concentrated ammonium hexafluorophosphate. The solution was applied to a C18 silica column. Water was used to wash away excess salt. The pure product 10 (as the $PF_6$ salt) was then eluted using acetonitrile.

Example 8

Synthesis of Ligand 11

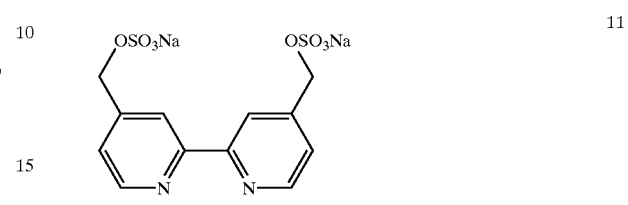

Ligand 11 was prepared by the reaction of 4,4'-bis-hydroxymethyl-2,2'-bipyridine (prepared by the sodium borohydride reduction of 4,4'-bis-carboxy-2,2-bipyridine dimethyl ester in refluxing ethanol) with sulfur trioxide pyridine complex ($SO_3pyr$). $SO_3pyr$ (107 mg) was added to 35.3 mg of 4,4'-bis-hydroxymethyl-2,2'-bipyridine in 0.75 mL of DMF. After 1.5 hours, the product was precipitated with chloroform and redissolved in water. The aqueous solution was washed with chloroform, neutralized with NaOH solution, and lyophilized to a powder. The product was purified by reverse phase HPLC using a C18 column and a gradient of acetonitrile in water containing 0.1% TFA.

Example 9

Synthesis of Complex 12

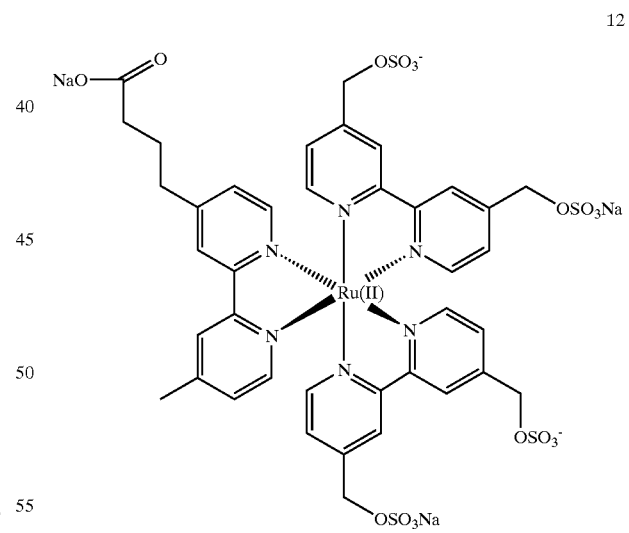

$RuCl_3$ hydrate (11.7 mg) was combined with 37.6 mg of ligand 11 in 75 mL of 4:1 methanol/water. The mixture was refluxed for 4 hours. The ligand 4-(4-methyl-2,2-bipyridine-4'-yl)-butyric acid (10.3 mg) was added and the mixture refluxed overnight. The solution was filtered and the filtrate concentrated by rotary evaporation. The product was purified by reverse phase chromatography using a gradient of acetonitrile in water and silica gel chromatography using methanol in acetonitrile as eluent.

Example 10

Synthesis of Complex 13

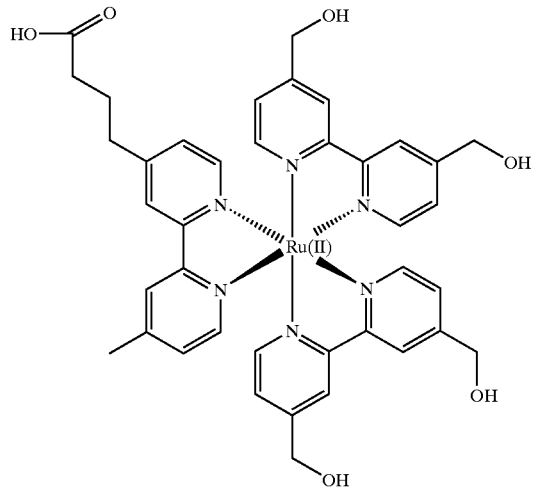

The ligand 4,4'-bis-hydroxymethyl-2,2'-bipyridine (58.7 mg) was combined with 58.1 mg of the complex of the ligand 4-(4-methyl-2,2-bipyridine-4'-yl)-butyric acid with $RuCl_3$ (see Example 2) in 50 mL of 1:1 methanol/water. The solution was refluxed overnight. The solution was then filtered and concentrated under vacuum. The product was dissolved in 5% acetonitrile/water, loaded on a column of C18 silica and eluted with 66% acetonitrile/water. The product was redissolved in 5% acetonitrile/water containing ammonium hexafluorphosphate, loaded onto C18 silica and eluted with 40% acetonitrile/water to give the pure complex in 45% yield.

Example 11

Synthesis of Complex 14

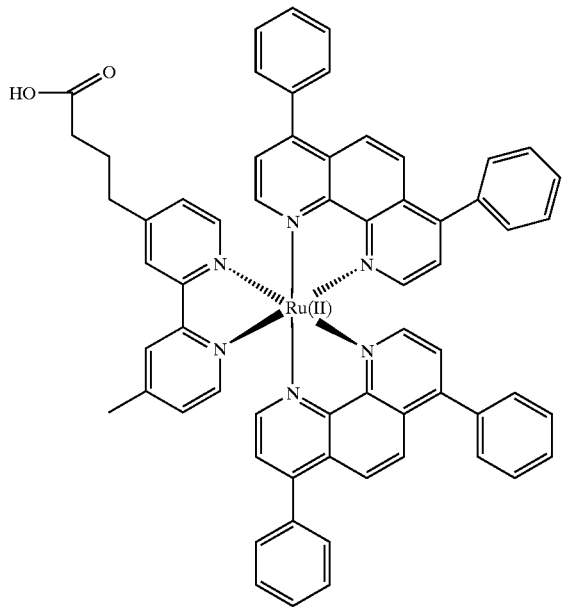

$RuCl_3$ hydrate was combined with two equivalents of 4,7-diphenylphenanthroline in DMF and refluxed overnight to give the bis-diphenylphenanthroline ruthenium dichloride intermediate as a black solid precipitate. The precipitate was collected by filtration, dried and combined with one equivalent of 4-(4-methyl-2,2-bipyridine-4'-yl)-butyric acid in 1:1 dioxane/water and refluxed overnight. The product was purified by reverse phase HPLC on C18 silica using a gradient of acetonitrile in water containing 0.1% TFA.

Example 12

Synthesis of Complex 15

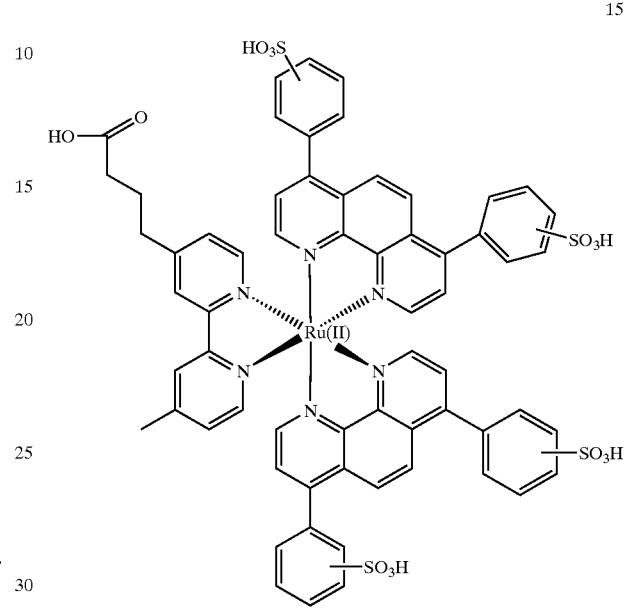

Complex 15 was prepared from 4,7-diphenyl-1,10-phenanthrolinedisulfonic acid (sodium salt) and [4-(4-methyl-2,2-bipyridine-4'-yl)-butyric acid]$RuCl_3$ using a procedure analogous to that which was reported above for the preparation of complex 2, except that purification was achieved by a single reverse phase HPLC purification using a C18 silica column and a gradient of acetonitrile in water containing 0.1% TFA.

Example 13

Synthesis of Ligand 16

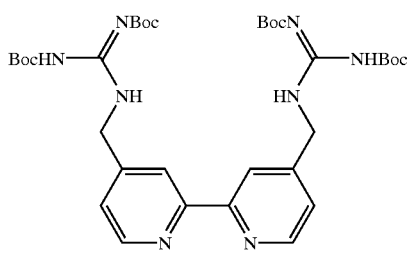

The ligand 4,4'-bis-hydroxymethyl-2,2'-bipyridine (108 mg) was combined with 520 mg of N,N'-bis-butyloxycarbonyl-guanidine and 393 mg of triphenylphosphine in 20 mL of 1:1 THF/toluene and cooled down to 0 C. Diisopropyl azodicarboylate (300 uL) was added over the course of 30 min. The mixture was stirred for 3 hours at 0 C. and 3 hours at room temperature. The reaction was quenched with 5 mL of water and the solvent removed under vacuum. Trituration with a 1:1 mixture of methanol and acetonitrile gave a white solid. The product was used without further purification. The structure of the product is shown as having the guanidine linked to the bipyridine via the unprotected nitrogen; linkage may have occurred via one of the protected nitrogens.

Example 14

Synthesis of Complex 17

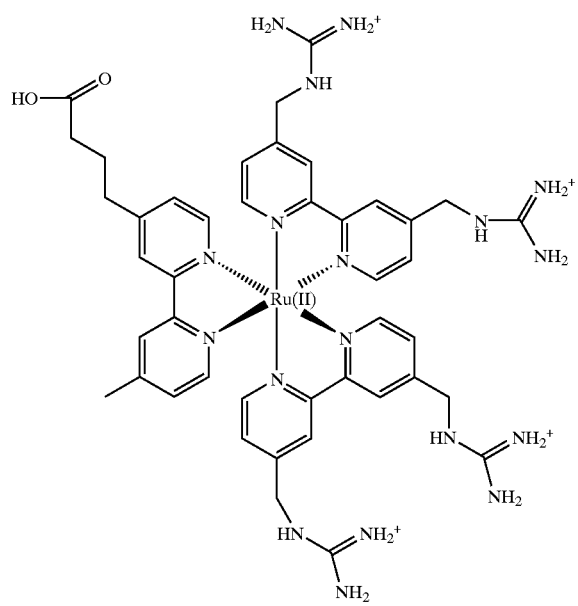

17

Ligand 16 (28.8 mg) was deprotected in 0.8 mL of 1:1 TFA/CH$_2$Cl$_2$. The solvent was removed under reduced vacuum and the deprotected ligand was used without further purification. The deprotected ligand was combined with the complex [4-(4-methyl-2,2-bipyridine-4'-yl)-butyric acid]Ru(II)(DMSO)$_2$Cl$_2$ (prepared by the overnight reaction of 4.8 mg of 4-(4-methyl-2,2-bipyridine-4'-yl)-butyric acid with 10.2 mg of Ru(DMSO)$_4$Cl$_2$ in 0.6 mL of methanol at room temperature) in 1.0 mL of ethanol and the reaction mixture was refluxed for 4 hours. The product was purified by ion exchange on SP-Sephadex C25 using a gradient of TFA in water and by reverse phase chromatography on reverse phase silica using an acetonitrile/water mixture containing 0.1% TFA as the eluent.

Example 15

Synthesis of Complex 18

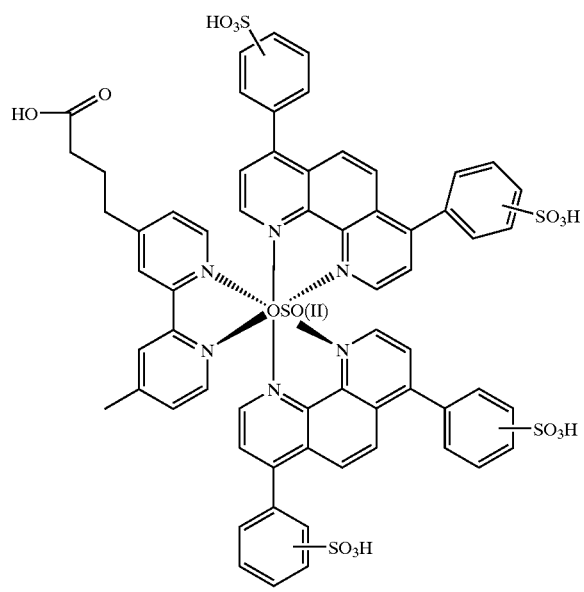

18

A mixture was prepared combining 1 g of (NH$_4$)$_2$OsCl$_2$ and 4,7-diphenyl-1,10-phenanthrolinedisulfonic acid (sodium salt) in 40 mL of 3 N HCl. The mixture was heated for 2 hours at 80 C. The solution was cooled and aqueous potassium carbonate was added until the pH reached ~9. The solution was concentrated under vacuum to dryness. Another equivalent of 4,7-diphenyl-1,10-phenanthrolinedisulfonic acid (sodium salt) was added in 20 mL of DMF. The solution was refluxed for 8 hr. After cooling, 200 mg of sodium dithionite was added in a small amount of water. The solution was concentrated under vacuum to ~10 mL after which the bis-ECL diphenylphenanthroline osmium dichloride intermediate was precipitated by the addition of acetone. The material was purified once more by precipitating the product from methanol by the addition of acetone.

A portion (266 mg) of the bis-diphenylphenanthroline osmium dichloride intermediate was combined with 60 mg of 4-(4-methyl-2,2-bipyridine-4'-yl)-butyric acid in 1:1 dioxane/water and refluxed for 18 hours. The solution was concentrated to dryness under vacuum and the residue redissolved in 10 mL of water. After addition of 200 mg of ammonium hexafluorophosphate, the solution was again concentrated to dryness and the residue was washed with 10 mL portions of acetonitrile. The product was purified by on reverse phase silica using methanol as the eluent.

Example 16

Synthesis of NHS Esters

The NHS ester of [4-(4-methyl-2,2-bipyridine-4'-yl)-butyric acid]Ru(II)[bpy]$_2$ (Complex 19) was obtained in purified form (NHS TAG, IGEN International) or was prepared in crude form from the corresponding carboxylic acid (Complex 20) by one of the methods described below. The NHS ester-containing complex 3 was made in purified form according to Example 3 or was prepared in crude form from complex 2 by one of the methods described below. NHS esters could be prepared in crude form under aprotic conditions or in water. Typically, aprotic conditions were used if possible. Water soluble complexes that were insoluble in typical aprotic solvents were prepared under aqueous conditions.

Aprotic conditions: The carboxylic acid containing complex was dissolved in methylene chloride to which was added a small excess of NHS and EDC. Some complexes that were not soluble in methylene chloride were reacted in acetonitrile or DMF or mixtures of these solvents with methylene chloride. After allowing the reaction to go to completion (as determined by HPLC or TLC), the solvent was removed under vacuum and the crude product was redissolved in DMF or DMSO to provide a stock solution for use in labeling reactions.

Aqueous conditions: To a 20 mM aqueous solution of the carboxylic acid-containing complex was added, in order of addition: i) 100 mM morpholino-ethanesulfonic acid (MES) buffer, pH 6.0, 50 mM NHS and 200 mM EDC HCl. The reaction was incubated from 15–30 minutes. The NHS ester product could be used as is. In some experiments, excess EDC was removed immediately after the preparation of the NHS ester by one of the following methods: i) purification of the product by size exclusion chromatography on Sephadex G-15 using water as the eluent; ii) passage of the product through a short column of SP-Sephadex C25 in the sodium form and elution with water or iii) loading of the product on a reverse phase chromatography medium and elution with water/acetonitrile. NHS ester made under one of these aqueous conditions was used immediately after preparation/purification (as described in Example 17).

Example 17

Labeling of Antibodies with NHS Esters

Antibodies were dissolved in PBS-1 buffer (150 mM potassium phosphate, 150 mM NaCl, pH 7.8) at concentrations greater than or equal to 2 mg/mL. ECL labels functionalized with NHS esters (prepared as described in Example 16) were added in water, DMF or DMSO (the final concentration of organic solvent should remain <20%) and the reaction was allowed to proceed for at least 2 hours at room temperature. The labeled proteins were purified by size exclusion chromatography on Sephadex G-25 (positively charged or neutral complexes) or Sephadex G-50 (negatively charged complexes). A variety of molar ratios of label to protein were generally tried since the efficiency of the coupling reaction could vary from label to label. The average number of labels per protein in the purified product was determined by using a calorimetric protein assay (BCA Assay or Coomassie Blue Assay, Pierce Chemicals) to determine the concentration of protein and the visible absorbance (typically at 455 nm for ruthenium-based labels) to determine the concentration of labels.

Example 18

A Comparison of Sandwich Immunoassays on Carbon Electrodes Using Antibodies Labeled with Complexes 20, 8, and 10

Plastic composite electrodes comprising carbon nanotubes (fibrils) dispersed in ethylene-co-vinyl acetate (EVA) were treated with an ammonia/nitrogen plasma so as to expose fibrils on the surface and introduce amine groups. An immobilized layer of streptavidin was introduced by treating the surface with SMCC (Pierce Chemical) and then reacting the surface with streptavidin (labeled with Traut's reagent to introduce thiol groups).

Sandwich immunoassays for α-fetoprotein (AFP) were carried out using 3/16" disks of the streptavidin-coated electrodes as solid phase supports and using antibodies, antibody diluents and calibrator diluents from the Elecsys AFP Assay (Roche Diagnostics). The Roche kit uses a biotin-labeled capture antibody and a detection antibody labeled with complex 20. To compare the labels of the invention, the labeled detection antibody of the kit was replaced with the same antibody but labeled with varying amounts of labels 20, 8, and 10 as described in Example 17. The streptavidin-coated electrode was contacted with the capture antibody, one of the labeled detection antibodies and a sample containing calibrator diluent (an artificial serum substitute containing bovine serum albumin and bovine IgG) spiked with 1864 ng/mL AFP. A negative control was also run using unspiked calibrator diluent. The assay mixtures were incubated over the electrodes to allow the sandwich complex to form after which the disks were washed with phosphate buffer and transferred to an ECL cell. ECL was measured by contacting the composite electrode with a solution containing tripropylamine (ORIGEN Assay Buffer, IGEN) and scanning the potential at the composite electrode to ~2.3 V.

FIG. 1 shows the non-specific signal (i.e., the signal in the absence of analyte) and the specific signal (the difference between the signal in the presence of analyte and the signal in the absence of analyte). The figure shows that labels 8 (presenting negatively charged phosphonate ester groups) and 10 (presenting neutral hydrophilic carboxamide groups) gave roughly the same specific signal as the conventional ECL label 20 and that the specific signal increased roughly linearly with the number of labels per protein. The labels showed significant and unexpected differences, however, in the amount of non-specific binding. The non-specific signal of label 20 increased exponentially with the number of labels per protein. By contrast, label 10 presenting neutral hydrophilic carboxamide groups showed less NSB and label 8 presenting negatively charged showed negligible NSB even at high numbers of labels per protein. Assay signal (S) as well as assay signal to background (S/B) can be improved by using label 8 because the number of labels per antibody can be increased (relative to conventional labels) without increasing NSB signals. The peak S/B measured with label 8 was greater than twice that measure with label 20. Using the optimal ratios of label to protein (as determined by S/B), the signal measured with label 8 was eight times greater than that measured with label 20.

Example 19

A Comparison of Sandwich Immunoassays on Carbon Electrodes Using Antibodies Labeled with Complexes 20, 2, 15, 12, 17 and 15

Figure 2:
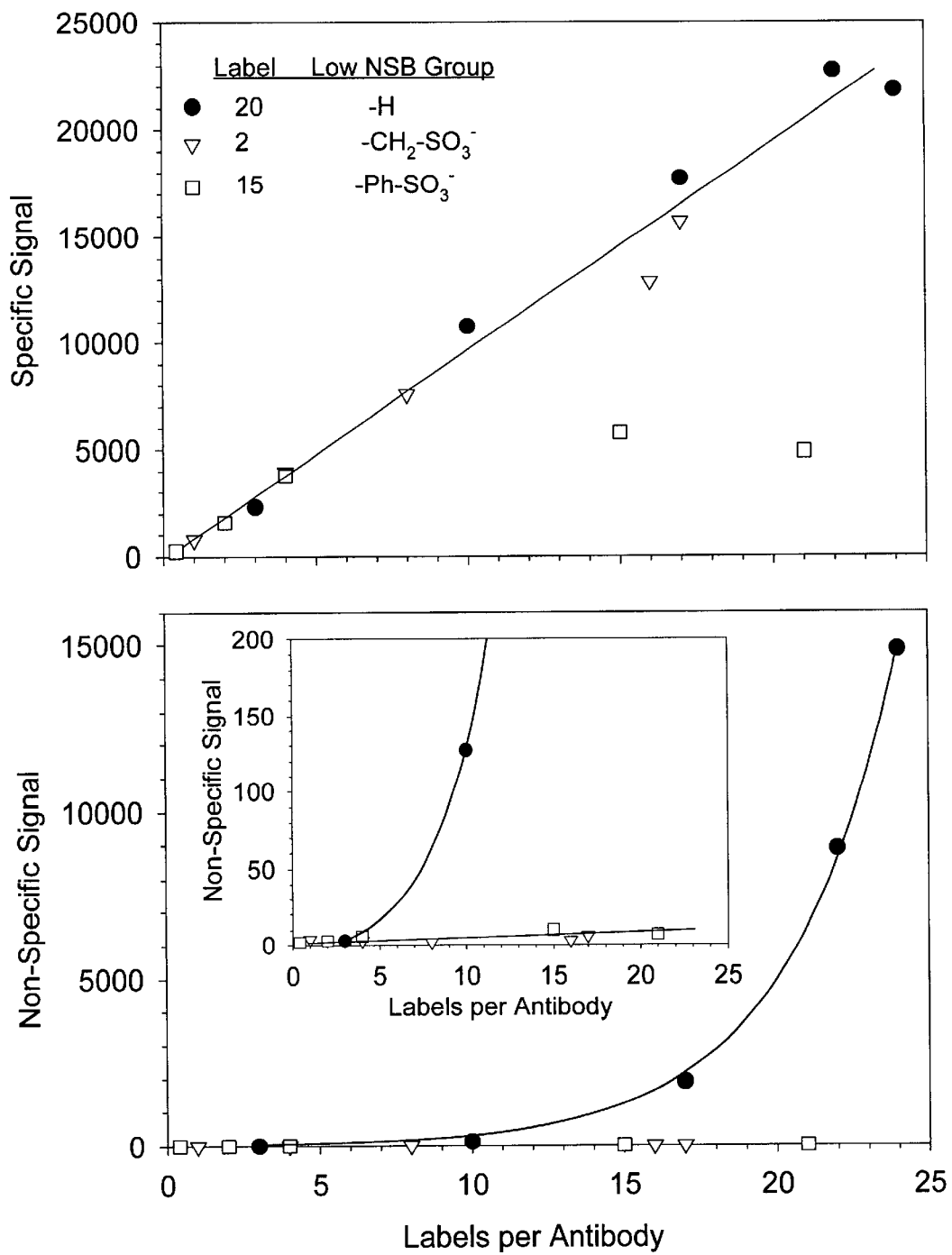
FIG. 2 shows the results of a comparison of ECL-based sandwich immunoassays on carbon composite electrodes using antibodies labeled with complexes 20, 2, 15, 12, 17 and 15. The figure shows the non-specific and specific signals as a function of the number of labels per antibody.

AFP assays were carried out as described in Example 18 except that the capture antibody was directly adsorbed on oxygen plasma treated fibril-EVA composite electrodes prior to conducting the assay and the calibrators (0 and 2200 ng/mL) were prepared in human serum. FIG. 2 shows that the specific signals from antibodies labeled with complexes 20, 2, and 15 were roughly similar except for antibodies highly labeled with the bathophenanthroline containing complex 15; we hypothesize that at high labeling ratios the large planar aromatic structure was able to either sterically block binding or denature the antibody and affect its activity. As also observed in Example 18, FIG. 2 shows that the non-specific signals from antibodies labeled with complexes having negatively charged ligands were low even at high numbers of labels per antibody, while the non-specific signal from the conventional label 20 went up exponentially with number of labels per antibody. The optimized S/B obtained using label 2 was greater than 5 times the optimized S/B obtained with label 20. Using the optimal ratios of label to protein (as determined by S/B), the signal measured with label 2 was more than three times greater than that measured with label 20. In similar assays (data not shown), antibodies labeled with a complex presenting sulfate groups (complex 12) behaved similarly to those labeled with complex 2. Antibodies labeled with the Os analog of complex 15, in general, showed similar low non-specific binding although the specific signals tended to be roughly 30–50% of the Ru complex. Antibodies labeled with the non-sulfonated version of complex 15 (i.e., complex 14), in general, gave higher backgrounds and lower signals even at low ratios of label to protein. We hypothesize that the highly hydrophobic complex interfered with antibody function. In similar assays, the highly positively charged complex 17 gave extremely high non-specific signals (at ~5–6 labels per antibody, the non-specific signal was more than 100 times the non-specific signal from antibodies labeled with complex 2). This result shows that the excellent behavior of the negatively charged complexes is not simply due to having hydrophilic charged groups but that the sign of the charge is important. We hypothesize that complex 17 may find use in some selected applications where assays are carried out near highly positively charged surfaces (the positive charge would be beneficial in those conditions for preventing NSB). Complex 17 and other complexes having ligand 16 may also find use in applications requiring the adsorption of a luminescent label to an electrode (e.g., in luminescence-based sensors, ECL-based HPLC detectors or ECL displays using ECL labels adsorbed on electrodes or in films, such as Nafion films, deposited on an electrode).

Example 20

A Comparison of Sandwich Immunoassays on Magnetic Particles Using Antibodies Labeled with Complexes 20 and 2

Figure 3:
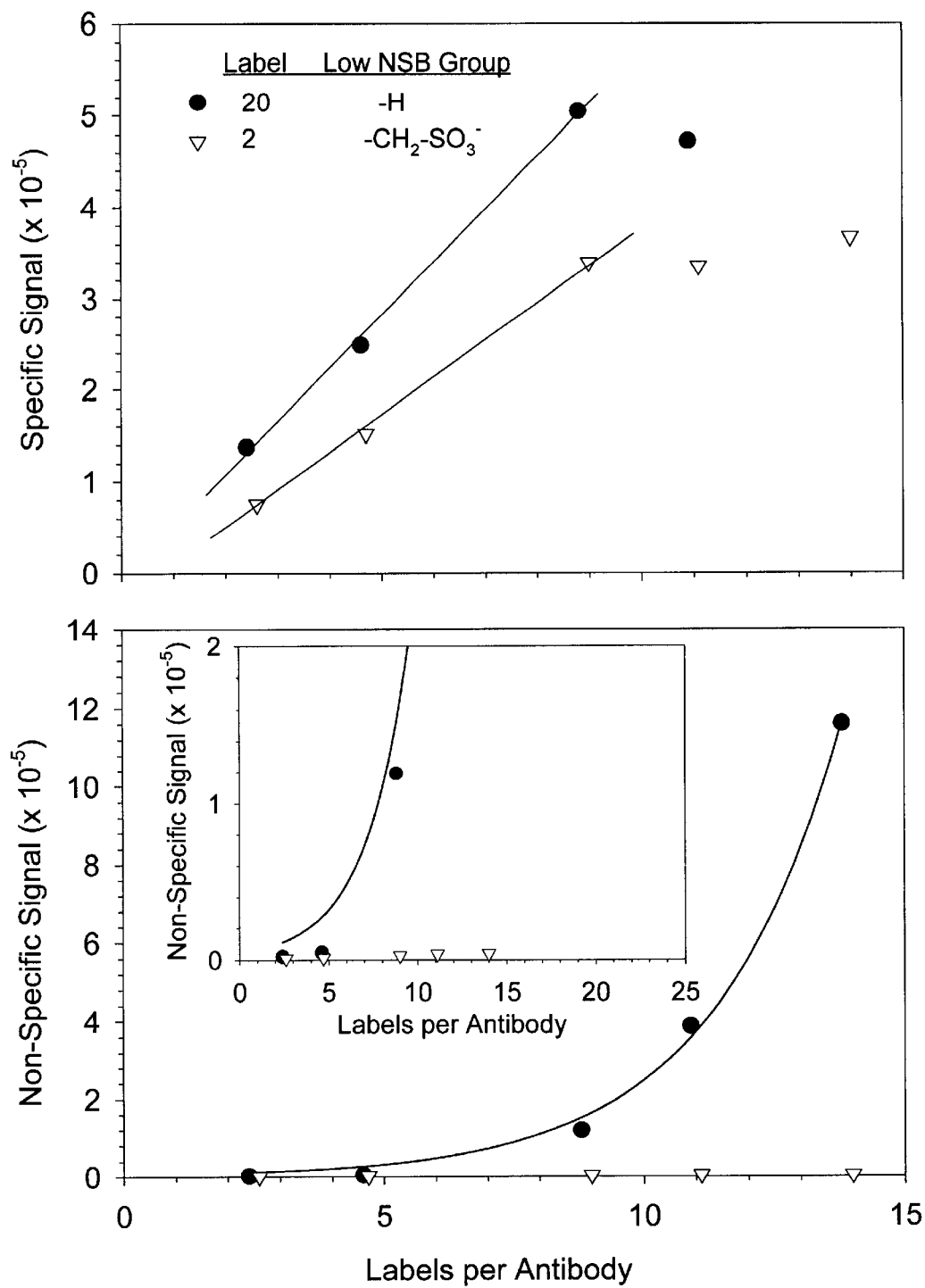
FIG. 3 shows the results of a comparison of ECL-based sandwich immunoassays carried out on magnetic particles using antibodies labeled with complexes 20 and 2. The figure shows the non-specific and specific signals as a function of the number of labels per antibody.

AFP assays were carried out using the Elecsys AFP Assay (Roche Diagnostics) reagents except that the standard detection antibody was replaced with the same antibody but labeled with varying amounts of complexes 20 or 2. A sample (0.007 mL) containing a known concentration of AFP (0 or 1000 ng/mL) in a buffered solution containing blocking proteins was combined with 0.035 mL of the biotin-labeled capture antibody (0.0045 mg/mL) and 0.035 mL of the detection antibody (0.012 mg/mL). The reaction mixture was incubated at room temperature for 15 minutes after which 0.035 mL of streptavidin-coated magnetic particles (0.72 mg/mL) and 0.139 mL of a buffered solution of tripropylamine (ORIGEN Assay Buffer, IGEN International) was added. The reaction mixture was incubated for an additional 15 minutes, after which the suspension was analyzed using an ORIGEN M-8 Instrument (IGEN International) and ECL detection. FIG. 3 shows that label 2 gave slightly less specific signal than label 20, but drastically less non-specific signal, especially for heavily labeled antibodies. The optimized S/B obtained using label 2 was more than two times the optimized S/B obtained with label 20.

What is claimed is:

1. A bipyridine or phenanthroline ligand selected from the group consisting of:

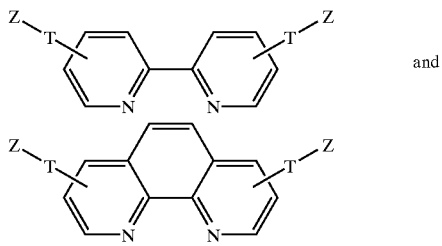

and wherein,
said bipyridine or phenanthroline ligand is not substituted at the bipyridine or phenanthroline ring nitrogens;
T is an alkyl linker having, optionally, one or more chain carbons substituted by a heteroatom;
Z is —$SO_3^-$, —$SO_3H$, —$OSO_3^-$, —$OSO_3H$, —$PO_3^{2-}$, —$OPO_3H^-$, —$OPO_3H_2$, —$OP(R)O_2^-$ —$OP(R)O_2H$, —$[NHC(NH_2)_2]^+$, or —$NHC(NH)NH_2$; and
R is alkyl.

2. The ligand of claim 1, wherein T is —$(CH_2)_n$— and n is an integer between 1 and 5.

3. The ligand of claim 2, wherein Z is —$SO_3^-$ or —$SO_3H$.

4. The ligand of claim 2, wherein Z is —$OSO_3^-$ or —$OSO_3H$.

5. The ligand of claim 2, wherein Z is —$OPO_3^{2-}$, —$OPO_3H^-$, —$OPO_3H_2$, —$OP(Me)O_2^-$ or —$OP(Me)O_2H$.

6. The ligand of claim 2, wherein Z is —$[NHC(NH_2)_2]^+$ or —$NHC(NH)NH_2$.

7. A luminescent metal complex comprising the ligand of claim 2 and a metal atom, the metal atom being bound to the ring nitrogens of the ligand.

8. A method for conducting a luminescence-based assay comprising the steps of:
(a) using a luminescent metal complex comprising a ligand selected from the group consisting of

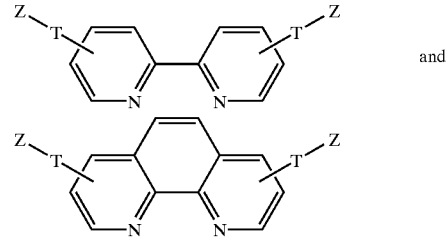

and wherein,
T is an alkyl linker having, optionally, one or more chain carbons substituted by a heteroatom;
Z is —$SO_3^-$, —$SO_3H$, —$OSO_3^-$, —$OSO_3H$, —$PO_3^{2-}$, —$PO_3H^-$, —$PO_3H_2$, —$OPO_3^{2-}$, —$OPO_3H^-$, —$OPO_3H_2$, —$OP(R)O_2^-$, —$OP(R)O_2H$, —$[NHC(NH_2)_2]^+$, or —$NHC(NH)NH_2$;
R is alkyl; and
said metal complex comprises a metal atom that is bound to the ring nitrogens of said ligand;
(b) inducing said metal complex to emit luminescence; and
(c) measuring the emitted luminescence.

9. A method as recited in claim 8, wherein said metal complex exhibits reduced non-specific binding in said assay relative to the analogous complex having Z=H.

10. A luminescent metal complex having the structure $M(L^1)_3$ wherein
M is Os or Ru; and
$L^1$ is a ligand selected from the group consisting of:

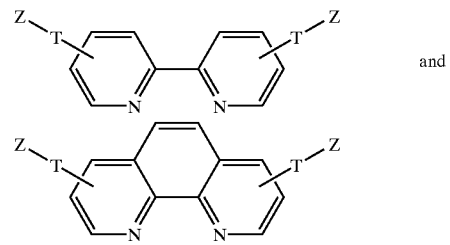

and wherein,
T is an alkyl linker having, optionally, one or more chain carbons substituted by a heteroatom;
Z is —$SO_3^-$, —$SO_3H$, —$OSO_3^-$, —$OSO_3H$, —$PO_3^{2-}$, —$PO_3H^-$, —$PO_3H_2$, —$OPO_3^{2-}$, —$OPO_3H^-$, —$OPO_3H_2$, —$OP(R)O_2^-$, —$OP(R)O_2H$, —$[NHC(NH_2)_2]^+$, or —$NHC(NH)NH_2$; and
R is alkyl.

11. A method for conducting a luminescence-based assay comprising the steps of:

(a) using a luminescent metal complex having the structure $M(L^1)_3$ wherein

M is Os or Ru; and $L^1$ is a ligand selected from the group consisting of:

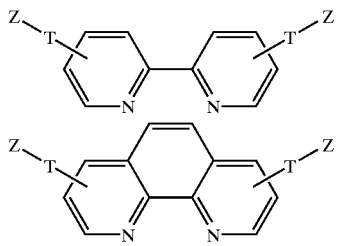 and wherein,

T is an alkyl linker having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl;

(b) inducing said metal complex to emit luminescence; and (c) measuring the emitted luminescence.

12. A method as recited in claim 11, wherein said metal complex exhibits reduced non-specific binding in said assay relative to the analogous complex having Z=H.

13. A luminescent metal complex having the structure $ML^1L^2_2$ wherein

M is Os or Ru;

$L^1$ is a substituted bipyridine or phenanthroline ligand having at least one substituent that can react with a biological material, binding reagent, enzyme substrate or other assay reagent so as to form a covalent linkage; and $L^2$ is a metal ligand selected from the group consisting of:

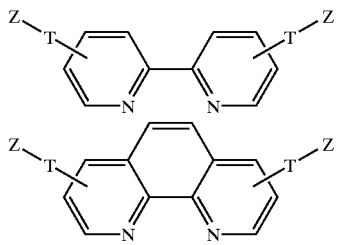 and wherein,

T is a linker group comprising an alkyl, alkenyl, alkynyl or phenyl linker, or a combination thereof, having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl.

14. The luminescent metal complex of claim 13, wherein $L^1$ is selected from the group consisting of

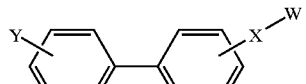 and

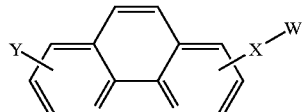

wherein,

X is a linker group comprising an alkyl, alkenyl, alkynyl or phenyl linker, or a combination thereof, having, optionally, one or more chain carbons substituted by a heteroatom;

Y is H or alkyl and

W is a substituent that can react with a biological material, binding reagent, enzyme substrate or other assay reagent so as to form a covalent linkage.

15. The luminescent metal complex of claim 13, wherein Z is —SO$_3$— or —SO$_3$H.

16. The luminescent metal complex of claim 13, Wherein Z is —OSO$_3$— or —OSO$_3$H.

17. The luminescent metal complex of claim 13, wherein Z is —PO$_3$H$^-$, —PO$_3$H$_2$, —OPO$_3^{2-}$, —OPO$_3$H$^-$, —OPO$_3$H$_2$, —OP(Me)O$_2^-$ or —OP(Me)O$_2$H.

18. The luminescent metal complex of claim 13, wherein Z is —[NHC(NH$_2$)$_2$]$^+$ or —NHC(NH)NH$_2$.

19. The luminescent metal complex of claim 13, wherein M is Os.

20. The luminescent metal complex of claim 13, wherein W is an activated carboxyl group.

21. The luminescent metal complex of claim 13, wherein W is a carboxylic acid group, an amine group, or a hydroxyl group.

22. A luminescent metal complex having the structure $ML^1L^2_2$ wherein

M is Os or Ru;

$L^1$ is selected from the group consisting of

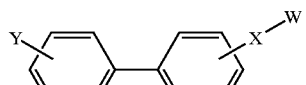 and

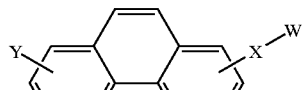

wherein,

X is an alkyl linker having, optionally, one or more chain carbons substituted by a heteroatom;

Y is H or alkyl and

W is a functional group that can react with a biological material, binding reagent, enzyme substrate or other assay reagent so as to form a covalent linkage; and L² is a metal ligand selected from the group consisting of:

[structures of bipyridine and phenanthroline with Z-T substituents]

wherein,
T is an alkyl linker having, optionally, one or more chain carbons substituted by a heteroatom; and
Z is —SO₃⁻ or —SO₃H.

23. The luminescent complex according to claim 22, wherein M is Ru.

24. The luminescent complex according to claim 22, wherein T is —(CH₂)ₙ—, X is —(CH₂)ₘ— and n and m are each integers between 1 and 5.

25. The luminescent complex of claim 22, wherein L² is a phenanthroline ligand substituted at the 4 and 7 positions or L² is a bypyridine ligand substituted at the 4 and 4' positions.

26. The luminescent metal complex of claim 22, wherein W is an activated carboxyl group.

27. The luminescent metal complex of claim 22, wherein W is a carboxylic acid group, an amino group, or a thiol group.

28. The luminescent metal complex of claim 22, wherein W is

[NHS ester structure]

29. A luminescent metal complex with the structure:

[Ru(II) complex structure with SO₃⁻, SO₃Na, NaO₃S groups and W substituent]

wherein W is a functional group that can react with a biological material, binding reagent, enzyme substrate or other assay reagent so as to form a covalent linkage.

30. The luminescent metal complex according to claim 29, wherein W is an activated carboxyl.

31. The luminescent complex according to claim 29, wherein W is a carboxyl group, an amino group, or a hydroxyl group.

32. The luminescent complex of claim 29, wherein W is

[NHS ester structure]

33. A labeled material comprising a luminescent metal complex having the structure

ML¹L²₂ wherein
M is Os or Ru;
L¹ is a substituted bipyridine or phenanthroline ligand having at least one substituent that is covalently linked to a biological material, binding reagent, enzyme substrate or other assay reagent; and
L² is a metal ligand selected from the group consisting of:

[structures of bipyridine and phenanthroline with Z-T substituents]

wherein,
T is a linker group comprising an alkyl, alkenyl, alkynyl or phenyl linker, or a combination thereof, having, optionally, one or more chain carbons substituted by a heteroatom;
Z is —SO₃⁻, —SO₃H, —OSO₃⁻, —OSO₃H, —PO₃²⁻, —PO₃H⁻, —PO₃H₂, —OPO₃²⁻, —OPO₃H⁻, —OPO₃H₂, —OP(R)O₂⁻, —OP(R)O₂H, —[NHC(NH₂)₂]⁺, or —NHC(NH)NH₂; and
R is alkyl.

34. The labeled material of claim 33, wherein L¹ is selected from the group consisting of

[structures of bipyridine and phenanthroline with Y and X-W-B substituents]

wherein,
X is a linker group comprising an alkyl, alkenyl, alkynyl or phenyl linker, or a combination thereof, having, optionally, one or more chain carbons substituted by a heteroatom;

Y is H or alkyl;

B is the biological material, binding reagent, enzyme substrate or other assay reagent; and W is a functional group that is linked to B.

35. The labeled material of claim 33, wherein Z is —SO$_3$— or —SO$_3$H.

36. The labeled material of claim 33, wherein Z is —OSO$_3$— or —OSO$_3$H.

37. The labeled material of claim 33, wherein Z is —PO$_3$H$^-$, —PO$_3$H$_2$, —OPO$_3^{2-}$, —OPO$_3$H$^-$, —OPO$_3$H$_2$, —OP(Me)O$_2^-$ or —OP(Me)O$_2$H.

38. The labeled material of claim 33, wherein Z is —[NHC(NH$_2$)$_2$]$^+$ or —NHC(NH)NH$_2$.

39. The labeled material of claim 33, wherein M is Os.

40. The labeled material of claim 33, wherein the complex exhibits less non-specific binding than the analogous complex in which Z is H.

41. The labeled material of claim 33, wherein said biological material, binding reagent, enzyme substrate or other assay reagent is selected from the group consisting of amino acids, nucleosides, nucleotides, proteins, peptides, peptidomimetics, nucleic acids, and peptide nucleic acids.

42. The labeled material of claim 41, wherein said biological material, binding reagent, enzyme substrate or other assay reagent is linked to five or more of said luminescent metal complexes.

43. The labeled material of claim 41, wherein said biological material, binding reagent, enzyme substrate or other assay reagent is linked to ten or more of said luminescent metal complexes.

44. A method for conducting a luminescence-based assay comprising the steps of:

(a) using a labeled material comprising a luminescent metal complex having the structure

wherein

M is Os or Ru;

L$^1$ is a substituted bipyridine or phenanthroline ligand having at least one substituent that is covalently linked to a biological material, binding reagent, enzyme substrate or other assay reagent; and L$^2$ is a metal ligand selected from the group consisting of:

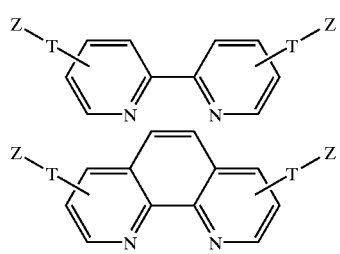

wherein,

T is a linker group comprising an alkyl, alkenyl, alkynyl or phenyl linker, or a combination thereof, having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl;

(b) inducing said metal complex to emit luminescence; and (c) measuring the emitted luminescence.

45. The method according to claim 44, wherein said labeled material exhibits reduced non-specific binding in said assay relative to the analogous labeled material having Z=H.

46. A labeled material comprising a luminescent metal complex having the structure

wherein

M is Os or Ru;

L$^1$ is selected from the group consisting of

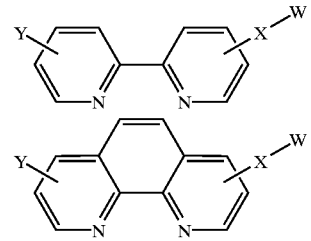

wherein,

X is an alkyl linker having, optionally, one or more chain carbons substituted by a heteroatom;

Y is H or alkyl and

W is a functional group that is linked to a biological material, binding reagent, enzyme substrate or other assay reagent; and L$^2$ is a metal ligand selected from the group consisting of:

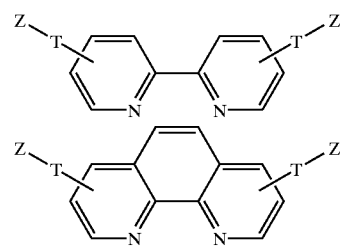

wherein,

T is an alkyl linker having, optionally, one or more chain carbons substituted by a heteroatom; and Z is —SO$_3^-$ or —SO$_3$H.

47. The labeled material according to claim 46, wherein M is Ru.

48. The labeled material according to claim 47, wherein T is —(CH$_2$)$_n$—, X is —(CH$_2$)$_m$— and n and m are each integers between 1 and 5.

49. The labeled material according to claim 47, wherein L$^2$ is a phenanthroline ligand substituted at the 4 and 7 positions or L$^2$ is a bypyridine ligand substituted at the 4 and 4' positions.

50. The labeled material according to claim 47, wherein the complex exhibits less non-specific binding than the analogous complex in which Z is H.

51. The labeled material according to claim 47, wherein said biological molecule, binding reagent, enzyme substrate or other assay reagent is selected from the group consisting of amino acids, nucleosides, nucleotides, proteins, peptides, peptidomimetics, nucleic acids, and peptide nucleic acids.

52. The labeled material according to claim 51, wherein said biological material, binding reagent, enzyme substrate or other assay reagent is linked to 5 or more of said luminescent metal complexes.

53. The labeled material according to claim 51, wherein said biological material, binding reagent, enzyme substrate or other assay reagent is linked to 10 or more of said luminescent metal complexes.

54. A method for conducting a luminescence-based assay comprising the steps of:

(a) using a labeled material comprising a luminescent metal complex having the structure $ML^1L^2_2$ wherein M is Os or Ru;

$L^1$ is selected from the group consisting of

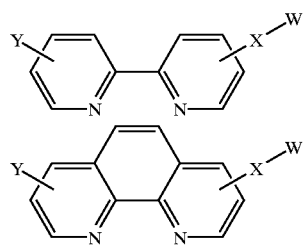

wherein,
X is an alkyl linker having, optionally, one or more chain carbons substituted by a heteroatom;
Y is H or alkyl; and
W is a functional group that is linked to a biological material, binding reagent, enzyme substrate or other assay reagent; and
$L^2$ is a metal ligand selected from the group consisting of:

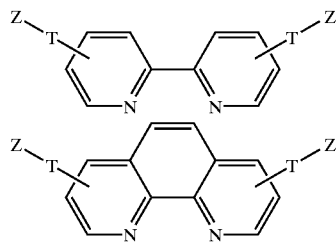

wherein,
T is an alkyl linker having, optionally, one or more chain carbons substituted by a heteroatom; and
Z is —$SO_3^-$ or —$SO_3H$;

(b) inducing said metal complex to emit luminescence; and (c) measuring the emitted luminescence.

55. The method according to claim 54, wherein said labeled material exhibits reduced non-specific binding in said assay relative to the analogous labeled material having Z=H.

56. A labeled material comprising a luminescent metal complex with the structure:

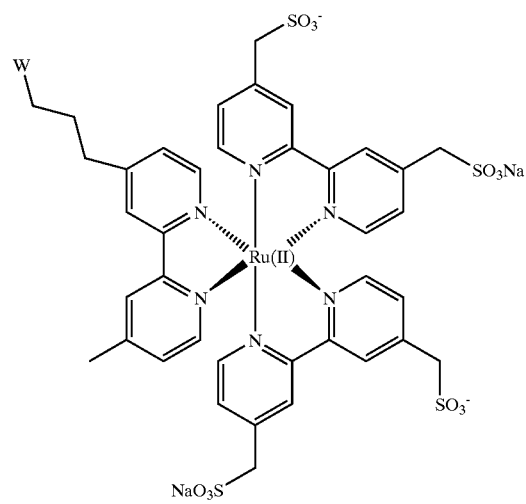

wherein W is a functional group that is linked to a biological material, binding reagent, enzyme substrate or other assay reagent.

57. The labeled material according to claim 56, wherein (i) W is —C(O)—, (ii) said biological material, binding reagent, enzyme substrate or other assay reagent is selected from the group consisting of amino acids, nucleosides, nucleotides, proteins, peptides, peptidomimetics, nucleic acids, and peptide nucleic acids and (iii) said biological material, binding reagent, enzyme substrate or other assay reagent is linked to W via an amide bond.

58. The labeled material according to claim 57, where said biological material, binding reagent, enzyme substrate or other assay reagent is linked to 5 or more of said luminescent metal complexes.

59. The labeled material according to claim 57, wherein said biological material, binding reagent, enzyme substrate or other assay reagent is linked to 10 or more of said luminescent metal complexes.

60. A method for conducting a luminescence-based assay comprising the steps of:

(a) using a labeled material comprising a luminescent metal complex having the structure

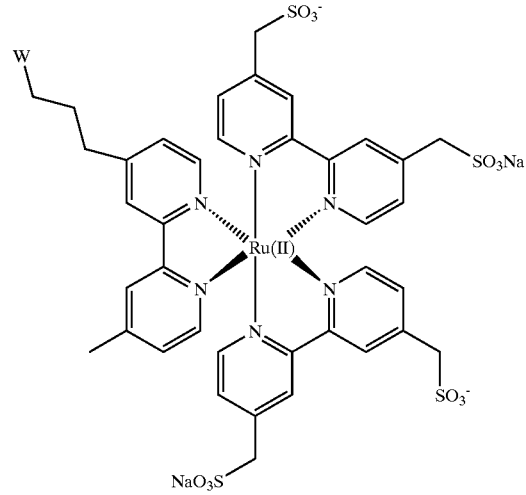

wherein W is a functional group that is linked to a biological material, binding reagent, enzyme substrate or other assay reagent;

(b) inducing said metal complex to emit luminescence; and (c) measuring the emitted luminescence.

61. The method according to claim 60, wherein said labeled material exhibits reduced non-specific binding in said assay relative to the analogous labeled material having Z=H.

62. A method of measuring an analyte, chemical activity or biological activity in a sample comprising the steps of i) contacting a sample containing the analyte, chemical activity, biological activity, a product of the biological activity or a product of the chemical activity with a luminescent metal complex; ii) inducing the metal complex to emit luminescence and iii) measuring the luminescence so as to detect or measure the chemical or biological activity; wherein said luminescent metal complex comprises a ligand selected from the group consisting of:

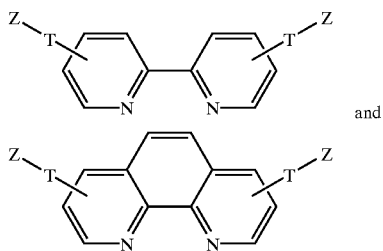

wherein,

T is an alkyl linker having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl.

63. The method of claim 62, wherein said labeled material exhibits less non-specific binding in said assay when compared to a labeled material having an analogous ligand that does not present non-specific binding reducing functional groups.

64. The method of claim 62, wherein said luminescence is electrochemiluminescence.

65. A method of measuring a labeled material comprising the steps of i) contacting the labeled material with a binding reagent and, optionally, a solid phase support; ii) forming a binding complex comprising the binding reagent, the labeled material, and, optionally, the solid phase support; iii) inducing the labeled material to emit luminescence and iv) measuring the emitted luminescence so as to measure the labeled material; wherein the labeled material is labeled with a luminescent metal complex comprising a ligand selected from the group consisting of

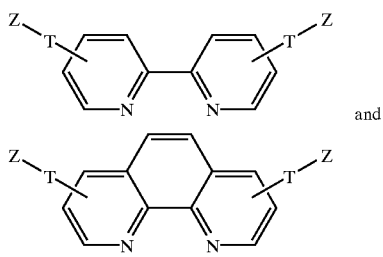

wherein,

T is an alkyl linker having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl.

66. The method of claim 65, wherein said labeled material is contacted with said solid phase and said binding complex is formed on said solid phase.

67. The method of claim 65, wherein said labeled material exhibits less non-specific binding in said assay when compared to an analogous labeled material having an analogous ligand that does not present non-specific binding reducing functional groups.

68. The method of claim 65, wherein said luminescence is electrochemiluminescence.

69. A method of measuring an analyte in a sample comprising the steps of i) contacting the sample with a labeled binding reagent and optionally a solid phase support; ii) forming a binding complex comprising the binding reagent, the analyte and, optionally, the solid phase support; iii) inducing labels in the labeled binding reagent to emit luminescence, preferably ECL and iv) measuring the emitted luminescence so as to measure the analyte in the sample; wherein said labeled binding reagent is labeled with a luminescent metal complex comprising a ligand selected from the group consisting of

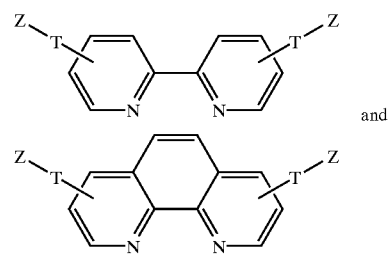

wherein,

T is an alkyl linker having, optionally, one or more chain carbons substituted by a heteroatom;

Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and R is alkyl.

70. The method of claim 69, wherein said labeled binding reagent is contacted with said solid phase and said binding complex is formed on said solid phase.

71. The method of claim 69, wherein said labeled binding reagent is contacted with said solid phase and said binding complex is formed on said solid phase.

72. The method of claim 69, wherein said labeled binding reagent exhibits less non-specific binding in said assay when compared to analogous labeled binding reagents that do not have labels that present non-specific binding reducing functional groups.

73. The method of claim 69, wherein said luminescence is electrochemiluminescence.

74. The method of claim 69, wherein said assay is a sandwich assay.

75. The method of claim 69, wherein said assay is a competitive assay.

76. A method of measuring an analyte in a sample comprising the steps of i) contacting the sample with a labeled analog of the analyte, a binding reagent and, optionally, a solid phase support; ii) forming a binding complex comprising the labeled analog of the analyte, the binding reagent and, optionally, the solid phase support; iii) inducing labels in the labeled analog of the analyte to emit luminescence, preferably ECL and iv) measuring the emitted luminescence so as to measure the analyte in the sample; wherein said labeled analog of the analyte is labeled with a luminescent metal complex comprising a ligand selected from the group consisting of

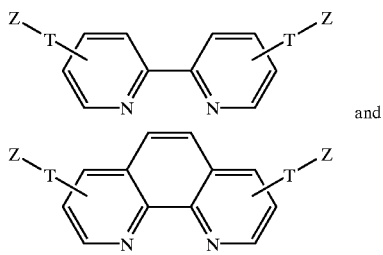

and wherein,
T is an alkyl linker having, optionally, one or more chain carbons substituted by a heteroatom;
Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and
R is alkyl.

77. The method of claim 76, wherein said labeled analog of the analyte is contacted with said solid phase and said binding complex is formed on said solid phase.

78. The method of claim 76, wherein said labeled analog of the analyte exhibits less non-specific binding in said assay when compared to analogous reagents that do not present non-specific binding reducing functional groups.

79. The method of claim 76, wherein said luminescence is electrochemiluminescence.

80. A method of improving a luminescence assay that employs a luminescent metal complex that contains a bipyridine, phenanthroline, substituted bipyridine or substituted phenanthroline ligand, said method comprising the step of substituting said ligand with a ligand selected from the group consisting of

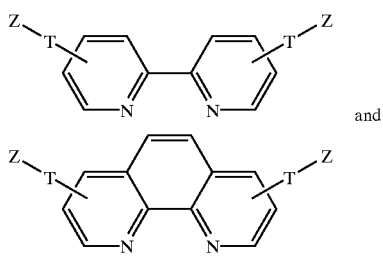

and wherein,
T is an alkyl linker having, optionally, one or more chain carbons substituted by a heteroatom;
Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and
R is alkyl.

81. The method of claim 80, wherein said replacement improves assay signal to background by a factor of two or greater.

82. A kit comprising, in one or more containers, a labeled material comprising a luminescent metal complex having the structure

ML$^1$L$^2_2$ wherein
M is Os or Ru;
L$^1$ is a substituted bipyridine or phenanthroline ligand having at least one substituent that is covalently linked to an assay-performance-substance; and
L$^2$ is a metal ligand selected from the group consisting of:

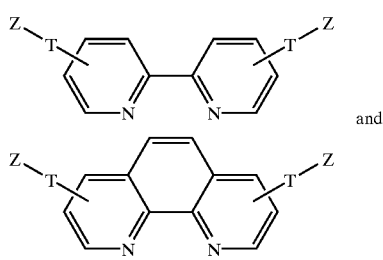

wherein,
T is a linker group comprising an alkyl, alkenyl, alkynyl or phenyl linker, or a combination thereof, having, optionally, one or more chain carbons substituted by a heteroatom;
Z is —SO$_3^-$, —SO$_3$H, —OSO$_3^-$, —OSO$_3$H, —PO$_3^{2-}$, —PO$_3$H$^-$, —PO$_3$H$_2$, —OPO$_3^{2-}$, —OPO$_3$H$^-$, —OPO$_3$H$_2$, —OP(R)O$_2^-$, —OP(R)O$_2$H, —[NHC(NH$_2$)$_2$]$^+$, or —NHC(NH)NH$_2$; and
R is alkyl; and
at least one assay component selected from the group consisting of:
(a) an electrochemiluminescence coreactant;
(b) one or more binding reagents;
(c) one or more pH buffers.

83. A kit according to claim 82, further comprising one or more additional assay components selected from the group consisting of:
(a) one or more blocking reagents;
(b) one or more preservatives;
(c) one or more stabilizing agents;
(d) one or more enzymes; and
(e) one or more detergents.

84. A labeled material comprising a luminescent metal complex having the structure

ML$^1$L$^2_2$ wherein
M is Os or Ru;
L$^1$ is a substituted bipyridine or phenanthroline ligand having at least one substituent that is covalently linked to an assay-performance-substance; and
L$^2$ is a metal ligand selected from the group consisting of:

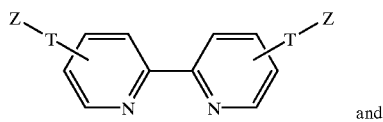

and

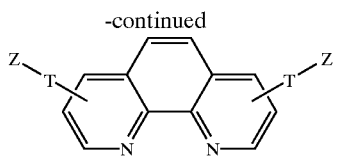

wherein,

T is a linker group comprising an alkyl, alkenyl, alkynyl or phenyl linker, or a combination thereof, having, optionally, one or more chain carbons substituted by a heteroatom;

Z is $-SO_3^-$, $-SO_3H$, $-OSO_3^-$, $-OSO_3H$, $-PO_3^{2-}$, $-PO_3H^-$, $-PO_3H_2$, $-OPO_3^{2-}$, $-OPO_3H^-$, $-OPO_3H_2$, $-OP(R)O_2^-$, $-OP(R)O_2H$, $-[NHC(NH_2)_2]^+$, or $-NHC(NH)NH_2$; and R is alkyl.

85. A labeled material according to claim 84, wherein said assay-performance-substance is selected from the group consisting of:
(a) added analyte of interest or added analogue of said analyte;
(b) a binding partner of said analyte or a binding partner of an analogue of said analyte; and
(c) a reactive component capable of binding with (a) or (b).

86. A composition of matter for use as a reagent in an assay comprising:
(a) a labeled material comprising a luminescent metal complex having the structure $ML^1L^2_2$ wherein M is Os or Ru;

$L^1$ is a substituted bipyridine or phenanthroline ligand having at least one substituent that is covalently linked to an assay-performance-substance; and $L^2$ is a metal ligand selected from the group consisting of:

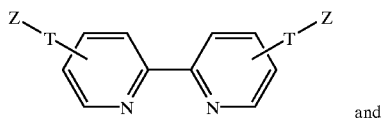

and

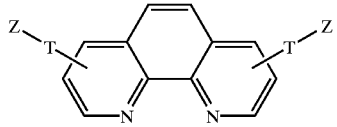

wherein,

T is a linker group comprising an alkyl, alkenyl, alkynyl or phenyl linker, or a combination thereof, having, optionally, one or more chain carbons substituted by a heteroatom;

Z is $-SO_3^-$, $-SO_3H$, $-OSO_3^-$, $-OSO_3H$, $-PO_3^{2-}$, $-PO_3H^{31}$, $-PO_3H_2$, $-OPO_3^{2-}$, $-OPO_3H^-$, $-OPO_3H_2$, $-OP(R)O_2^-$, $-OP(R)O_2H$, $-[NHC(NH_2)_2]^+$, or $-NHC(NH)NH_2$; and R is alkyl; and (b) at least one additional assay component selected from the group consisting of:
(i) electrolyte;
(ii) analyte of interest or an analog of the analyte of interest;
(iii) a binding partner of the analyte of interest or of its analog;
(iv) a reactive component capable of reacting with (ii) or (iii); and
(v) an ECL coreactant, provided, however, that no two components contained within any reagent composition are reactive with one another during storage so as to impair their function in the intended assay.

87. A composition of matter for the detection of an analyte of interest present in a sample, which composition comprises a labeled material comprising a luminescent metal complex having the structure $ML^1L^2_2$ wherein M is Os or Ru;

$L^1$ is a substituted bipyridine or phenanthroline ligand having at least one substituent that is covalently linked to an assay-performance-substance and $L^2$ is a metal ligand selected from the group consisting of:

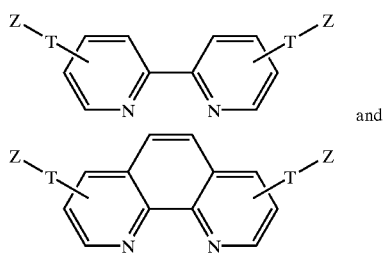

and wherein,

T is a linker group comprising an alkyl, alkenyl, alkynyl or phenyl linker, or a combination thereof, having, optionally, one or more chain carbons substituted by a heteroatom;

Z is $-SO_3^-$, $-SO_3H$, $-OSO_3^-$, $-OSO_3H$, $-PO_3^{2-}$, $-PO_3H^-$, $-PO_3H_2$, $-OPO_3^{2-}$, $-OPO_3H^-$, $-OPO_3H_2$, $-OP(R)O_2^-$, $-OP(R)O_2H$, $-[NHC(NH_2)_2]^+$, or $-NHC(NH)NH_2$; and R is alkyl, said assay-performance-substance being capable of binding to the analyte-of-interest or being bound to the analyte-of-interest.

88. A composition of matter according to claim 87, wherein said composition contains at least one additional substance selected from the group consisting of
(i) added analyte of interest or added analogue of said analyte;
(ii) a binding partner of said analyte or a binding partner of said analogue; and
(iii) a reactive component capable of binding with (i) or (ii).

89. The ligand of claim 3, wherein n=1.

90. A luminescent metal complex comprising the ligand of claim 89 and an osmium atom, the osmium atom being bound to the ring nitrogens of the ligand.

91. A luminescent metal complex comprising the ligand of claim 89 and a ruthenium atom, the ruthenium atom being bound to the ring nitrogens of the ligand.

92. The luminescent complex according to claim 22, wherein M is Os.

93. The labeled material of claim 35, wherein M is Os.

94. The labeled material of claim 46, wherein M is Os.

* * * * *

UNITED STATES PATENT AND TRADEMARK OFFICE
CERTIFICATE OF CORRECTION

PATENT NO.    : 6,808,939 B2
DATED         : October 26, 2004
INVENTOR(S)   : Sigal et al.

It is certified that error appears in the above-identified patent and that said Letters Patent is hereby corrected as shown below:

Column 27,
Line 59, after "-OP(R)O$_2^-$" insert -- , --.

Column 30,
Line 27, "Wherein" should read -- wherein --.

Column 34,
Lines 51, 54, 58 and 61, "claim 47," should read -- claim 46, --.

Column 41,
Line 57, "-PO$_3$H$^{31}$," should read -- -PO$_3$H$^-$, --.

Column 42,
Line 19, after "assay-performance-substance" insert -- ; --.

Signed and Sealed this

Fourth Day of January, 2005

JON W. DUDAS
*Director of the United States Patent and Trademark Office*